(12) United States Patent  (10) Patent No.: US 7,885,711 B2
Ben-Ezra et al.  (45) Date of Patent: Feb. 8, 2011

(54) VAGAL STIMULATION FOR ANTI-EMBOLIC THERAPY

(75) Inventors: Omry Ben-Ezra, Jerusalem (IL); Ehud Cohen, Ganei Tikva (IL); Tamir Ben-David, Tel-Aviv (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 17 days.

(21) Appl. No.: 10/560,654

(22) PCT Filed: Jun. 10, 2004

(86) PCT No.: PCT/IL2004/000496

§ 371 (c)(1),
(2), (4) Date: May 1, 2006

(87) PCT Pub. No.: WO2004/110550

PCT Pub. Date: Dec. 23, 2004

(65) Prior Publication Data

US 2006/0271115 A1 Nov. 30, 2006

Related U.S. Application Data

(63) Continuation-in-part of application No. 10/461,696, filed on Jun. 13, 2003, now Pat. No. 7,321,793.

(60) Provisional application No. 60/478,576, filed on Jun. 13, 2003.

(51) Int. Cl.
*A61N 1/362* (2006.01)
(52) U.S. Cl. ..................... 607/5; 607/4; 607/9; 607/14
(58) Field of Classification Search ..................... 607/4, 607/5, 9, 14
See application file for complete search history.

(56) References Cited

U.S. PATENT DOCUMENTS 3,411,507 A 11/1968 Wingrove (Continued)

FOREIGN PATENT DOCUMENTS

EP 0 688 577 12/1995

(Continued)

OTHER PUBLICATIONS

Bibevski, S. and Dunlap M.E:, (1999) "Ganglionic Mechanisms Contribute to Diminished Vagal Control in Heart Failure," Circulation, 99(22):2958-63.

(Continued)

*Primary Examiner*—Scott M Getzow
*Assistant Examiner*—Joseph M Dietrich
(74) *Attorney, Agent, or Firm*—John P. White; Cooper & Dunham LLP

(57) ABSTRACT

Apparatus (20) for treating a subject (30) suffering from spontaneous atrial fibrillation includes an electrode device (22), adapted to be coupled to a site of the subject (30) selected from the list consisting of: a vagus nerve (24) of the subject (30), an epicardial fat pad of the subject (30), a pulmonary vein of the subject (30), a carotid artery of the subject (30), a carotid sinus of the subject (30), a vena cava vein of the subject (30), and an internal jugular vein of the subject (30), and a control unit (32), adapted to drive the electrode device (22) to apply an electrical current to the site, and to configure the current to maintain the spontaneous AF for at least about 24 hours, so as to modify blood flow within the atria and reduce risk of thromboembolic events.

24 Claims, 5 Drawing Sheets

U.S. PATENT DOCUMENTS

| | | |
|---|---|---|
| 4,019,518 A | 4/1977 | Maurer et al. |
| 4,161,952 A | 7/1979 | Kinney et al. |
| 4,338,945 A | 7/1982 | Kosugi et al. |
| 4,392,496 A | 7/1983 | Stanton |
| 4,535,785 A | 8/1985 | van den Honert et al. |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples et al. |
| 4,608,985 A | 9/1986 | Crish et al. |
| 4,628,942 A | 12/1986 | Sweeney et al. |
| 4,632,116 A | 12/1986 | Rosen |
| 4,649,936 A | 3/1987 | Ungar et al. |
| 4,663,102 A | 5/1987 | Brenman et al. |
| 4,702,254 A | 10/1987 | Zabara |
| 4,739,764 A | 4/1988 | Lue et al. |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,042,497 A | 8/1991 | Shapland |
| 5,058,599 A | 10/1991 | Andersen |
| 5,069,680 A | 12/1991 | Grandjean |
| 5,170,802 A | 12/1992 | Mehra |
| 5,178,161 A | 1/1993 | Kovacs |
| 5,188,104 A | 2/1993 | Wernicke et al. |
| 5,199,428 A | 4/1993 | Obel et al. |
| 5,199,430 A | 4/1993 | Fang et al. |
| 5,203,326 A | 4/1993 | Collins |
| 5,205,285 A | 4/1993 | Baker |
| 5,215,086 A | 6/1993 | Terry et al. |
| 5,224,491 A | 7/1993 | Mehra |
| 5,243,980 A | 9/1993 | Mehra |
| 5,263,480 A | 11/1993 | Wernicke et al. |
| 5,282,468 A | 2/1994 | Klepinski |
| 5,292,344 A | 3/1994 | Douglas |
| 5,299,569 A | 4/1994 | Wernicke et al. |
| 5,314,495 A | 5/1994 | Kovacs |
| 5,330,507 A | 7/1994 | Schwartz et al. |
| 5,334,221 A | 8/1994 | Bardy |
| 5,335,657 A | 8/1994 | Terry et al. |
| 5,356,425 A | 10/1994 | Bardy et al. |
| 5,411,531 A | 5/1995 | Hill et al. |
| 5,423,872 A | 6/1995 | Cigaina |
| 5,437,285 A | 8/1995 | Verrier et al. |
| 5,454,840 A | 10/1995 | Krakovsky |
| 5,487,756 A | 1/1996 | Kallesoe |
| 5,507,784 A | 4/1996 | Hill et al. |
| 5,522,854 A | 6/1996 | Ideker et al. |
| 5,540,730 A | 7/1996 | Terry et al. |
| 5,540,734 A | 7/1996 | Zabara |
| 5,562,718 A | 10/1996 | Palermo |
| 5,571,150 A | 11/1996 | Wernicke et al. |
| 5,578,061 A | 11/1996 | Stroetmann et al. |
| 5,615,684 A | 4/1997 | Hagel et al. |
| 5,634,462 A | 6/1997 | Tyler et al. |
| 5,645,570 A | 7/1997 | Corbucci |
| 5,658,318 A | 8/1997 | Stroetmann et al. |
| 5,662,689 A | 9/1997 | Elsberry et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry et al. |
| 5,711,316 A | 1/1998 | Elsberry et al. |
| 5,716,385 A | 2/1998 | Mittal et al. |
| 5,755,750 A | 5/1998 | Petruska et al. |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,928,269 A * | 7/1999 | Alt ............... 607/5 |
| 5,938,584 A | 8/1999 | Ardito et al. |
| 6,006,134 A | 12/1999 | Hill et al. |
| 6,026,326 A | 2/2000 | Bardy |
| 6,038,476 A | 3/2000 | Schwartz |
| 6,058,328 A | 5/2000 | Levine et al. |
| 6,058,331 A | 5/2000 | King et al. |
| 6,066,163 A | 5/2000 | John |
| 6,073,048 A | 6/2000 | Kieval et al. |
| 6,086,525 A | 7/2000 | Davey et al. |
| 6,091,977 A | 7/2000 | Tarjan et al. |
| 6,091,992 A | 7/2000 | Bourgeois |
| 6,094,598 A | 7/2000 | Elsberry et al. |
| 6,097,984 A | 8/2000 | Douglas |
| 6,104,955 A | 8/2000 | Bourgeois |
| 6,104,956 A | 8/2000 | Naritoku et al. |
| 6,104,960 A | 8/2000 | Duysens et al. |
| 6,119,516 A | 9/2000 | Hock |
| H1905 H | 10/2000 | Hill |
| 6,134,470 A | 10/2000 | Hartlaub |
| 6,146,335 A | 11/2000 | Gozani |
| 6,161,029 A | 12/2000 | Spreigl et al. |
| 6,167,304 A | 12/2000 | Loos |
| 6,169,924 B1 | 1/2001 | Meloy et al. |
| 6,205,359 B1 | 3/2001 | Boveja |
| 6,230,061 B1 | 5/2001 | Hartung |
| 6,240,314 B1 | 5/2001 | Plicchi et al. |
| 6,256,537 B1 * | 7/2001 | Stoop et al. ............ 607/14 |
| 6,266,564 B1 | 7/2001 | Hill |
| 6,272,377 B1 | 8/2001 | Sweeney et al. |
| 6,292,695 B1 | 9/2001 | Webster et al. |
| 6,319,241 B1 | 11/2001 | King et al. |
| 6,341,236 B1 | 1/2002 | Osorio et al. |
| 6,356,784 B1 | 3/2002 | Lozano et al. |
| 6,366,813 B1 | 4/2002 | Dilorenzo |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,434,424 B1 | 8/2002 | Igel et al. |
| 6,449,507 B1 | 9/2002 | Hill et al. |
| 6,456,866 B1 | 9/2002 | Tyler |
| 6,463,328 B1 | 10/2002 | John |
| 6,473,644 B1 | 10/2002 | Terry et al. |
| 6,493,585 B2 | 12/2002 | Plicchi et al. |
| 6,511,500 B1 | 1/2003 | Rahme |
| 6,522,926 B1 | 2/2003 | Kieval et al. |
| 6,542,774 B2 | 4/2003 | Hill et al. |
| 6,564,096 B2 | 5/2003 | Mest |
| 6,571,122 B2 | 5/2003 | Schroeppel et al. |
| 6,587,727 B2 | 7/2003 | Osorio et al. |
| 6,600,956 B2 | 7/2003 | Maschino et al. |
| 6,610,713 B2 | 8/2003 | Tracey |
| 6,622,041 B2 | 9/2003 | Terry et al. |
| 6,628,987 B1 | 9/2003 | Hill et al. |
| 6,668,191 B1 | 12/2003 | Boveja |
| 6,671,556 B2 | 12/2003 | Osorio et al. |
| 6,684,105 B2 | 1/2004 | Cohen |
| 6,690,971 B2 | 2/2004 | Schauerte et al. |
| RE38,705 E | 2/2005 | Hill et al. |
| 6,865,416 B2 | 3/2005 | Dev et al. |
| 6,885,888 B2 | 4/2005 | Rezai et al. |
| 6,895,280 B2 | 5/2005 | Meadows et al. |
| 6,907,295 B2 | 6/2005 | Gross et al. |
| 6,928,320 B2 | 8/2005 | King |
| 6,934,583 B2 | 8/2005 | Weinberg et al. |
| 6,985,774 B2 | 1/2006 | Kieval et al. |
| 7,050,846 B2 | 5/2006 | Sweeney et al. |
| 7,076,299 B2 | 7/2006 | Thong |
| 7,076,307 B2 | 7/2006 | Boveja et al. |
| 7,079,891 B1 * | 7/2006 | Kroll ............ 607/4 |
| 7,136,700 B1 | 11/2006 | Province et al. |
| 7,142,917 B2 | 11/2006 | Fukui |
| 7,403,819 B1 | 7/2008 | Shelchuk et al. |

| | | |
|---|---|---|
| 2002/0029002 A1 | 3/2002 | Bardy |
| 2002/0035335 A1 | 3/2002 | Schauerte |
| 2002/0107553 A1 | 8/2002 | Hill et al. |
| 2002/0120304 A1 | 8/2002 | Mest |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050677 A1 | 3/2003 | Gross et al. |
| 2003/0078623 A1 | 4/2003 | Weinberg et al. |
| 2003/0100924 A1 | 5/2003 | Foreman et al. |
| 2003/0195574 A1 | 10/2003 | Osorio et al. |
| 2003/0216775 A1 | 11/2003 | Hill et al. |
| 2003/0229380 A1 | 12/2003 | Adams |
| 2003/0233129 A1 | 12/2003 | Matos |
| 2003/0236558 A1 | 12/2003 | Whitehurst et al. |
| 2004/0048795 A1 | 3/2004 | Ivanova et al. |
| 2004/0059392 A1 | 3/2004 | Parramon et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0162594 A1 | 8/2004 | King |
| 2004/0172075 A1 | 9/2004 | Shafer et al. |
| 2004/0199210 A1 | 10/2004 | Shelchuk |
| 2004/0215289 A1 | 10/2004 | Fukui |
| 2004/0243182 A1 | 12/2004 | Cohed et al. |
| 2004/0249416 A1 | 12/2004 | Yun et al. |
| 2004/0254612 A1 | 12/2004 | Ezra et al. |
| 2005/0131467 A1 | 6/2005 | Bojeva |
| 2005/0187584 A1 | 8/2005 | Denker et al. |
| 2005/0222644 A1 | 10/2005 | Killian et al. |
| 2006/0015153 A1 | 1/2006 | Gliner et al. |
| 2006/0047325 A1 | 3/2006 | Thimineur et al. |
| 2006/0052831 A1 | 3/2006 | Fukui |
| 2006/0064140 A1 | 3/2006 | Whitehurst et al. |
| 2006/0074450 A1 | 4/2006 | Boveja |
| 2006/0129205 A1 | 6/2006 | Boveja |
| 2006/0149337 A1 | 7/2006 | John |
| 2006/0167498 A1 | 7/2006 | DiLorenzo |
| 2007/0027487 A1 | 2/2007 | Mika et al. |

FOREIGN PATENT DOCUMENTS

| | | |
|---|---|---|
| EP | 0831954 | 4/1998 |
| WO | WO 01-10375 | 2/2001 |
| WO | WO 01-10432 | 2/2001 |
| WO | WO 01-26729 | 4/2001 |
| WO | WO 02-085448 | 10/2002 |

OTHER PUBLICATIONS

Bilgutay, A.M. et al., (1968) "Vagal Tuning. A New Concept In The Treatment of Supereantricular Arrhythmia, Angina Pectoris, and Heart Failure," *The Journal of Thoracic and Cardiovascular Surgery*, 56(1): 71-82.

Blumen, K.M. et al., (1990) "Parasympathetic Postganglionic Pathways to the Sinoatrial Node," The American Journal of Physiology, 259 (5 Pt 2):H1504-10.

Carlson, M.D. et al., (1992) "Selective Stimulation of Parasympathetic Nerve Fibers to the Human Sinoatrial Node," Circulation, 85: 1311-1317.

Chen, S. et al., (1998) "Intracardiac Stimulation of Human Parasympathetic Nerve Fibers Induces Negative Dromotropic Effects: Implication With The Lesions of Radiofrequency Catheter Ablation," *Journal of Cardiovascular Electrophysiology*, 9(3): 245-52.

Cooper, T.B. et al., (1980) "Neural Effects on Sinus Rate and Atriventricular Conduction Produced by Electrical Stimulation From A Transvenous Electrode Catheter in the Canine Right Pulmonary Artery," *Circulation Research*, 46: 48-57.

Cummings, J.E. et al., (1980) "Preservation of the Anterior Fat Pad Paradoxically Decreases The Incidence of Postoperative Atrial Fibrillation in Humans," *Journal of the American College of Cardiology*, 43(6): 994-1000.

Friedrichs, G., (2000) "Experimental Models of Atrial Fibrillation/Flutter," Journal of Pharmacological and Toxicological Methods, 43: 117-123.

Furukawa, Y. et al., (1989) "Differential Blocking Effects of Atropine and Gallamine on Negative Chronotropic and Dromotropic Responses to Vagus Stimulation in Anesthetized Dogs," *Journal of Pharmacology and Experimental Therapeutics*, 251 (3): 797-802.

Fuster, V. and Ryden, L.E., (2001) "ACC/AHA/ESC Guidelines For The Management of Patients With Atrial Fibrillation," *Journal of the American College of Cardiology*, 38(4): 1231-66.

Garrigue, S. et al., (1998) "Post-ganglionic Vagal Stimulation of The Atrioventricular Node Reduces Ventricular Rate During Atrial Fibrillation," *Pacing and Clinical Electrophysiology*, 21(4), Part II, 878.

Goldberger, J.J. et al., (1999) "New Technique For Vagal Nerve Stimulation," Journal of Neuroscience Methods, 91(1-2): 109-114.

Hjalmarson, A., (1999) "Prevention of Sudden Cardiac Death With Beta Blockers," Clinical Cardiology, 22 Suppl 5: V11-5.

Jideus, L., (2001) "Atrial Fibrillation After Coronary Artery Bypass Surgery. A Study of Causes and Risk Factors," *Comprehensive Summaries of Uppsala Dissertations from the Faculty of Medicine*, 1093: 1-56.

Kwan, H. et al., (2001) "Cardiovascular Adverse Drug Reactions During Initiation of Antiarrhythmic Therapy For Atrial Fibrillation," *Canadian Journal of Hospital Pharmacists*, 54(1): 11-14.

Li, D. et al., (1999) "Promotion of Atrial Fibrillation by Heart Failure in Dogs. Atrial Remodeling of a Different Sort," Circulation, 100(1): 87-95.

Manfredi, M., (1970) "Differential Block of Conduction of Larger Fibers in Peripheral Nerve by Direct Current," Archives italiennes de biologie, 108(1): 52-71.

Mazgalev, T.N., "AV Nodal Physiology," Hearth Rhythm Society, www.HRSonline.com.

Page, P.L. et al., (1995) "Regional Distribution of Atrial Electrical Changes Induced by Stimulation of Extracardiac and Intracardiac Neural Elements," *The Journal off Thoracic and Cardiovascular Surgery*, 109(2): 377-88.

Rijkhoff, N.J.M. and Sinkjçr, T., (1999) "Selective Stimulation of Small Diameter Nerve Fibers in a Mixed Bundle," *Proceedings of The Annual Project Meeting Sensations/Neuros and Mid Term Review Meeting Neuros*, p. 20-21.

Waninger, M.S. et al., (2000) "Electrophysiological Control of Ventricular Rate During Atrial Fibrillation," Pacing and Clinical Physiology, 23(8): 1236-44.

Zhang, Y. et al., (2002) "Optimal Ventricular Rate Slowing During Atrial Fibrillation by Feedback AV Nodal-Selective Vagal Stimulation," *American Journal of Physiology: Heart and Circulatory Physiology*, 282(3): H1102-10.

Schaldach, M., (1992) "New Concepts in Electrotherapy of the Heart," Electrotherapy of the Heart, Springer Verlag Heidelberg: 210-214.

Nov. 1, 2007 Office Action issued by the U.S. Patent and Trademark Office in connection with U.S. Appl. No. 10/205,475.

Jones, J. F. X. et al., (1995) "Heart Rate Responses to Selective Stimulation of Cardiac Vagal C Fibres in Anaesthetized Cats, Rats and Rabbits," Journal of Physiology, 489(1): 203-214.

Jones, J.F.X. et al., (1998) "Activity of C Fibre Cardiac Vagal Efferents in Anaesthetized Cats and Rats," Journal of Physiology, 507(3) 869-880.

Office Action issued Jun. 27, 2008 during the prosecution of Applicants' U.S. Appl. No. 10/205,475.

Fang, Zi-Ping and Mortimer, J. Thomas, (1991) "Selective activation of small motor axons by quasitrapezoidal current pulses," *IEEE Transactions on Biomedical Engineering*, 38(2):168-174.

Armour, J.A. et al. eds., (1994) *Neurocardiology*. Oxford University Press: 60-64.

Martin, P.J. et al., (1983) "Phasic effects of repetitive vagal stimulation on atrial contraction." Circulation Research: vol. 52(6): 657-663.

Office Action issued Nov. 9, 2009 during the prosecution of Applicants' U.S. Appl. No. 11/064,446.

Office Action issued Dec. 9, 2008 during the prosecution of Applicants' U.S. Appl. No. 11/978,379.

Moreira, D.A.R. et al., (1989) "Chronic rapid atrial fibrillation: use to permit control of ventricular rate in order to treat tachycard ia induced cardiomyopathy." *Pacing Clin. Electrophysiol.*: 12(5): 761-775.

Office Action, issued Jun. 24, 2009, in connection with U.S. Appl. No. 11/978,379, filed Oct. 29, 2007.

Office Action, issued Aug. 6, 2009, in connection with U.S. Appl. No. 10/205,475, filed Jul. 24, 2002.

Office Action, issued Aug. 21, 2009, in connection with U.S. Appl. No. 11/975,240, filed Oct. 17, 2007.

Office Action, issued Aug. 25, 2009, in connection with U.S. Appl. No. 11/975,241, filed Oct. 17, 2007.

Morillo et al., "Chronic Rapid Atrial Pacing. Structural, functional, and electrophysiological characteristics of a new model of sustained atrial fibrillation," *Circulation*, 1995, 91(5), 1588-1595.

Office Action, issued Feb. 5, 2010, in connection with U.S. Appl. No. 11/974,951, filed Oct. 16, 2007.

Office Action, issued Mar. 15, 2010, in connection with U.S. Appl. No. 11/724,899, filed Mar. 16, 2007.

Office Action, issued Apr. 6, 2010, in connection with U.S. Appl. No. 11/977,291, filed Oct. 23, 2007.

Office Action, issued Jun. 1, 2010, in connection with U.S. Appl. No. 11/975,407, filed Oct. 19, 2007.

Office Action, issued Jun. 23, 2010, in connection with U.S. Appl. No. 11/978,379, filed Oct. 29, 2007.

Office Action, issued Jun. 29, 2010, in connection with U.S. Appl. No. 11/064,446, filed Feb. 22, 2005.

Office Action, issued Jun. 30, 2010, in connection with U.S. Appl. No. 11/977,923, filed Oct. 25, 2007.

* cited by examiner

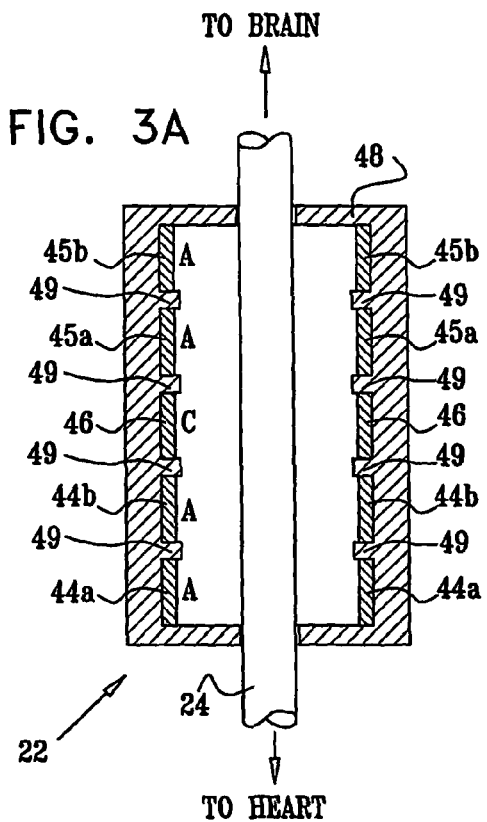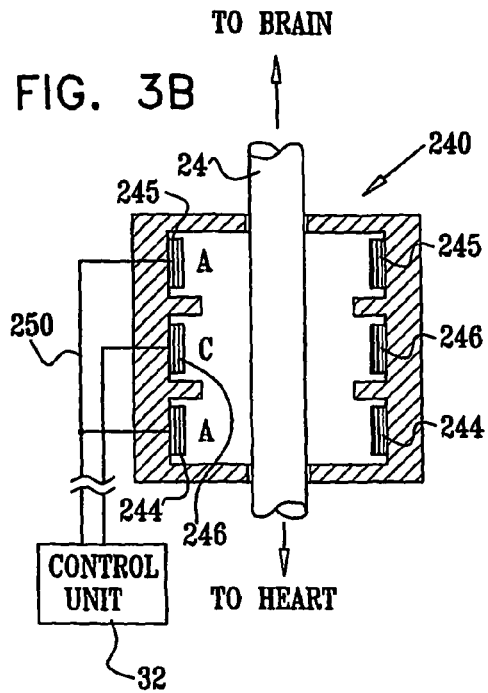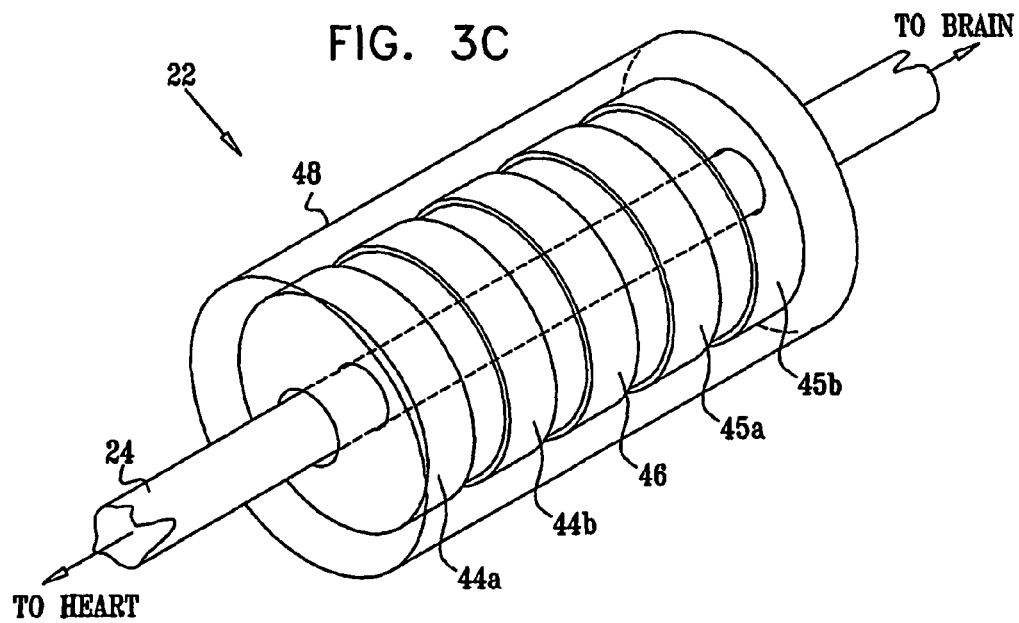

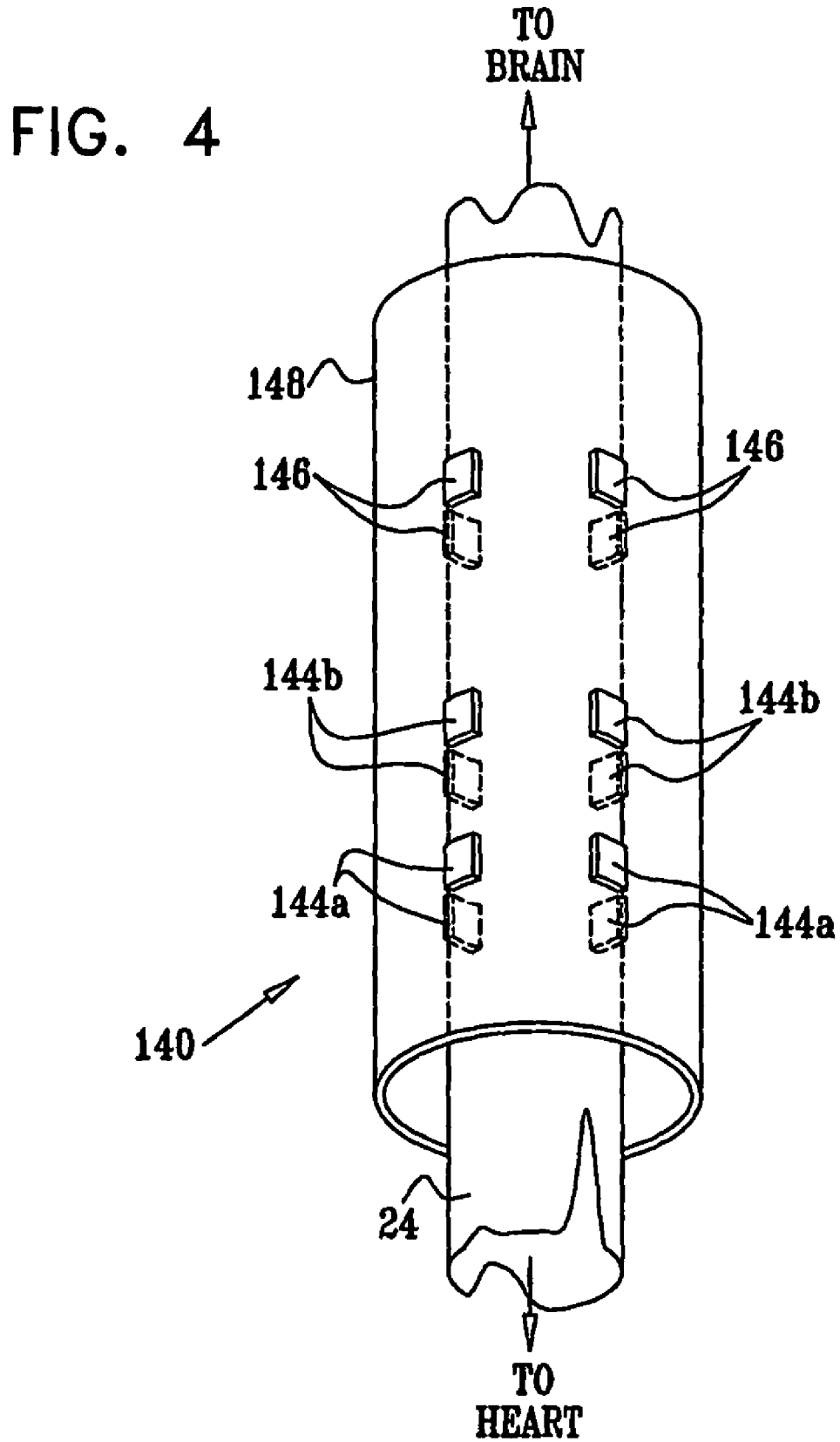

VAGAL STIMULATION FOR ANTI-EMBOLIC THERAPY

CROSS-REFERENCES TO RELATED APPLICATIONS

This application is a §371 national stage of PCT International Application No. PCT/IL2004/000496, filed Jun. 10, 2004, which (a) claims priority from and is a continuation-in-part of U.S. Ser. No. 10/461,696, filed Jun. 13, 2003 now U.S. Pat. No. 7,321,793, and (b) claims priority of U.S. Provisional Application No. 60/478,576, filed Jun. 13, 2003. Both of these applications are assigned to the assignee of the present application and are hereby incorporated herein by reference in their entireties.

FIELD OF THE INVENTION

The present invention relates generally to treating patients by application of electrical signals to selected tissue, and specifically to methods and apparatus for stimulating tissue for treating patients suffering from atrial fibrillation and/or from increased risk of thromboembolic events.

BACKGROUND OF THE INVENTION

The use of nerve stimulation for treating and controlling a variety of medical, psychiatric, and neurological disorders has seen significant growth over the last several decades, including for treatment of heart conditions. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic stimulation from the right and left vagus nerves. Low vagal nerve activity is considered to be related to various arrhythmias, including tachycardia, ventricular accelerated rhythm, and rapid atrial fibrillation. Stimulation of the vagus nerve has been proposed as a method for treating various heart conditions, including atrial fibrillation and heart failure. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Atrial fibrillation is a condition in which the atria of the heart fail to continuously contract in synchrony with the ventricles of the heart. During fibrillation, the atria undergo rapid and unorganized electrical depolarization, so that no contractile force is produced. The ventricles, which normally receive contraction signals from the atria (through the atrio-ventricular (AV) node), are inundated with signals, typically resulting in a rapid and irregular ventricular rate. Because of this rapid and irregular rate, the patient suffers from reduced cardiac output, a feeling of palpitations, and/or increased risk of thromboembolic events.

Current therapy for atrial fibrillation includes cardioversion and rate control. Cardioversion is the conversion of the abnormal atrial rhythm into normal sinus rhythm. This conversion is generally achieved pharmacologically or electrically. Rate control therapy is used to control the ventricular rate, while allowing the atria to continue fibrillation. This is generally achieved by slowing the conduction of signals through the AV node from the atria to the ventricles.

Bilgutay et al., in "Vagal tuning: a new concept in the treatment of supraventricular arrhythmias, angina pectoris, and heart failure," J. Thoracic Cardiovas. Surg. 56(1):71-82, July, 1968, which is incorporated herein by reference, studied the use of a permanently-implanted device with electrodes to stimulate the right vagus nerve for treatment of supraventricular arrhythmias, angina pectoris, and heart failure. Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats. The authors further studied the use of the implanted device in conjunction with the administration of Isuprel, a sympathomimetic drug. They found that Isuprel retained its inotropic effect of increasing contractility, while its chronotropic effect was controlled by the vagal stimulation: "An increased end diastolic volume brought about by slowing of the heart rate by vagal tuning, coupled with increased contractility of the heart induced by the inotropic effect of Isuprel, appeared to increase the efficiency of cardiac performance" (p. 79).

An article by Moreira et al., entitled, "Chronic rapid atrial pacing to maintain atrial fibrillation: Use to permit control of ventricular rate in order to treat tachycardia induced cardiomyopathy," Pacing Clin Electrophysiol, 12(5):761-775 (May 1989), which is incorporated herein by reference, describes the acute induction of atrial fibrillation with rapid atrial pacing, and an associated reduction in ventricular rate with digitalis therapy. Different treatment protocols are described to induce and maintain atrial fibrillation, in order to bring a patient with NYHA class III-IV congestive heart failure to a more moderate NYHA class II.

An article by Preston et al., entitled, "Permanent rapid atrial pacing to control supraventricular tachycardia," Pacing Clin Electrophysiol, 2(3):331-334 (May 1979), which is incorporated herein by reference, describes a patient who had continuous supraventricular tachycardia with a ventricular rate of about 170. The arrhythmia was refractory to drugs and DC countershock, and did not convert with atrial pacing. Rapid atrial stimulation (pacing at 300-400/min) controlled the ventricular rate by simulating atrial fibrillation. This therapy was used on a permanent basis for more than five months.

U.S. Pat. No. 6,473,644 to Terry, Jr. et al., which is incorporated herein by reference, describes a method for treating patients suffering from heart failure to increase cardiac output, by stimulating or modulating the vagus nerve with a sequence of substantially equally-spaced pulses by an implanted neurostimulator. The frequency of the stimulating pulses is adjusted until the patient's heart rate reaches a target rate within a relatively stable target rate range below the low end of the patient's customary resting heart rate.

The effect of vagal stimulation on heart rate and other aspects of heart function, including the relationship between the timing of vagal stimulation within the cardiac cycle and the induced effect on heart rate, has been studied in animals. For example, Zhang Y et al., in "Optimal ventricular rate slowing during atrial fibrillation by feedback AV nodal-selective vagal stimulation," Am J Physiol Heart Circ Physiol 282:H1102-H1110 (2002), describe the application of selective vagal stimulation by varying the nerve stimulation intensity, in order to achieve graded slowing of heart rate. This article is incorporated herein by reference.

The following articles and book, which are incorporated herein by reference, may be of interest:

Levy M N et al., in "Parasympathetic Control of the Heart," Nervous Control of Vascular Function, Randall W C ed., Oxford University Press (1984)

Levy M N et al. ed., Vagal Control of the Heart: Experimental Basis and Clinical Implications (The Bakken Research Center Series Volume 7), Futura Publishing Company, Inc., Armonk, N.Y. (1993)

Randall W C ed., Neural Regulation of the Heart, Oxford University Press (1977), particularly pages 100-106.

Armour J A et al. eds., Neurocardiology, Oxford University Press (1994)

Perez M G et al., "Effect of stimulating non-myelinated vagal axon on atrio-ventricular conduction and left ventricular function in anaesthetized rabbits," Auton Neurosco 86 (2001)

Jones, J F X et al., "Heart rate responses to selective stimulation of cardiac vagal C fibres in anaesthetized cats, rats and rabbits," J Physiol 489 (Pt 1):203-14 (1995)

Wallick D W et al., "Effects of ouabain and vagal stimulation on heart rate in the dog," Cardiovasc. Res., 18(2):75-9 (1984)

Martin P J et al., "Phasic effects of repetitive vagal stimulation on atrial contraction," Circ. Res. 52(6):657-63 (1983)

Wallick D W et al., "Effects of repetitive bursts of vagal activity on atrioventricular junctional rate in dogs," Am J Physiol 237(3):H275-81 (1979)

Fuster V and Ryden L E et al., "ACC/AHA/ESC Practice Guidelines—Executive Summary," J Am Coll Cardiol 38(4):1231-65 (2001)

Fuster V and Ryden L E et al., "ACC/AHA/ESC Practice Guidelines—Full Text," J Am Coll Cardiol 38(4):1266i-12661xx (2001)

Morady F et al., "Effects of resting vagal tone on accessory atrioventricular connections," Circulation 81(1):86-90 (1990)

Waninger M S et al., "Electrophysiological control of ventricular rate during atrial fibrillation," PACE 23:1239-1244 (2000)

Wijffels M C et al., "Electrical remodeling due to atrial fibrillation in chronically instrumented conscious goats: roles of neurohumoral changes, ischemia, atrial stretch, and high rate of electrical activation," Circulation 96(10):3710-20 (1997)

Wijffels M C et al., "Atrial fibrillation begets atrial fibrillation," Circulation 92:1954-1968 (1995)

Goldberger A L et al., "Vagally-mediated atrial fibrillation in dogs: conversion with bretylium tosylate," Int J Cardiol 13(1):47-55 (1986)

Takei M et al., "Vagal stimulation prior to atrial rapid pacing protects the atrium from electrical remodeling in anesthetized dogs," Jpn Circ J 65(12):1077-81 (2001)

Friedrichs G S, "Experimental models of atrial fibrillation/flutter," J Pharmacological and Toxicological Methods 43:117-123 (2000)

Hayashi H et al., "Different effects of class Ic and III antiarrhythmic drugs on vagotonic atrial fibrillation in the canine heart," Journal of Cardiovascular Pharmacology 31:101-107 (1998)

Morillo C A et al., "Chronic rapid atrial pacing. Structural, functional, and electrophysiological characteristics of a new model of sustained atrial fibrillation," Circulation 91:1588-1595 (1995)

Lew S J et al., "Stroke prevention in elderly patients with atrial fibrillation," Singapore Med J 43(4):198-201 (2002)

Higgins C B, "Parasympathetic control of the heart," Pharmacol. Rev. 25:120-155 (1973).

Hunt R, "Experiments on the relations of the inhibitory to the accelerator nerves of the heart," J. Exptl. Med. 2:151-179 (1897)

Billette J et al., "Roles of the AV junction in determining the ventricular response to atrial fibrillation," Can J Physiol Pharmacol 53(4)575-85 (1975)

Stramba-Badiale M et al., "Sympathetic-Parasympathetic Interaction and Accentuated Antagonism in Conscious Dogs," American Journal of Physiology 260 (2Pt 2):H335-340 (1991)

Garrigue S et al., "Post-ganglionic vagal stimulation of the atrioventricular node reduces ventricular rate during atrial fibrillation," PACE 21(4), 878 (Part 11) (1998)

Kwan H et al., "Cardiovascular adverse drug reactions during initiation of antiarrhythmic therapy for atrial fibrillation," Can J Hosp Pharm 54:10-14 (2001)

Jidéus L, "Atrial fibrillation after coronary artery bypass surgery: A study of causes and risk factors," Acta Universitatis Upsaliensis, Uppsala, Sweden (2001)

Feliciano L et al., "Vagal nerve stimulation during muscarinic and beta-adrenergic blockade causes significant coronary artery dilation," Cardiovasc Res 40(1):45-55 (1998)

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia. U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken.

U.S. Pat. NO. 5,330,507 to Schwartz, which is incorporated herein by reference, describes a cardiac pacemaker for preventing or interrupting tachyarrhythmias and for applying pacing therapies to maintain the heart rhythm of a patient within acceptable limits. The device automatically stimulates the right or left vagus nerves as well as the cardiac tissue in a concerted fashion dependent upon need. Continuous and/or phasic electrical pulses are applied. Phasic pulses are applied in a specific relationship with the R-wave of the ECG of the patient.

European Patent Application EP 0 688 577 to Holmström et al., which is incorporated herein by reference, describes a device to treat atrial tachyarrhythmia by detecting arrhythmia and stimulating a parasympathetic nerve that innervates the heart, such as the vagus nerve.

U.S. Pat. Nos. 5,690,681 and 5,916,239 to Geddes et al., which are incorporated herein by reference, describe closed-loop, variable-frequency, vagal-stimulation apparatus for control of ventricular rate during atrial fibrillation. The apparatus stimulates the left vagus nerve, and automatically and continuously adjusts the vagal stimulation frequency as a function of the difference between actual and desired ventricular excitation rates. In an alternative embodiment, the apparatus automatically adjusts the vagal stimulation frequency as a function of the difference between ventricular excitation rate and arterial pulse rate in order to eliminate or minimize pulse deficit.

US Patent Application Publication 2003/0040774 to Terry et al., which is incorporated herein by reference, describes a device for treating patients suffering from congestive heart failure. The device includes an implantable neurostimulator for stimulating the patient's vagus nerve at or above the cardiac branch with an electrical pulse waveform at a stimulating rate sufficient to maintain the patient's heart beat at a rate well below the patient's normal resting heart rate, thereby allowing rest and recovery of the heart muscle, to increase in coronary blood flow, and/or growth of coronary capillaries. A metabolic need sensor detects the patient's current physical state and concomitantly supplies a control signal to the neurostimulator to vary the stimulating rate. If the detection indicates a state of rest, the neurostimulator rate reduces the patient's heart rate below the patient's normal resting rate. If the detection indicates physical exertion, the neurostimulator rate increases the patient's heart rate above the normal resting rate.

US Patent Publication 2003/0045909 to Gross et al., which is assigned to the assignee of the present patent application and is incorporated herein by reference, describes apparatus for treating a heart condition of a subject, including an electrode device, which is adapted to be coupled to a vagus nerve of the subject. A control unit is adapted to drive the electrode device to apply to the vagus nerve a stimulating current, which is capable of inducing action potentials in a therapeutic direction in a first set and a second set of nerve fibers of the vagus nerve. The control unit is also adapted to drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

US Patent Publication 2003/0229380 to Adams et al., which is incorporated herein by reference, describes techniques for electrically stimulating the right vagus nerve in order to reduce the heart rate of a patient suffering from conditions such as chronic heart failure, ischemia, or acute myocardial infarction. The amount of energy of the stimulation may be determined in accordance with a difference between the patient's actual heart rate and a maximum target heart rate for the patient. Delivery of energy is preferably synchronized with the detection of a P-wave. Automatic adjustment of the target heart rate may be based on current day and/or time of day information, and patient physical activity. The voltage, pulse width, or number of pulses in the stimulation may be controlled.

U.S. Pat. No. 5,203,326 to Collins, which is incorporated herein by reference, describes a pacemaker which detects a cardiac abnormality and responds with electrical stimulation of the heart combined with vagus nerve stimulation. The vagal stimulation frequency is progressively increased in one-minute intervals, and, for the pulse delivery rate selected, the heart rate is described as being slowed to a desired, stable level by increasing the pulse current.

U.S. Pat. No. 6,511,500 to Rahme, which is incorporated herein by reference, describes various aspects of the effects of autonomic nervous system tone on atrial arrhythmias, and its interaction with class III antiarrhythmic drug effects.

U.S. Pat. No. 5,199,428 to Obel et al., which is incorporated herein by reference, describes a cardiac pacemaker for detecting and treating myocardial ischemia. The device automatically stimulates the vagal nervous system as well as the cardiac tissue in a concerted fashion in order to decrease cardiac workload and thereby protect the myocardium.

U.S. Pat. No. 5,334,221 to Bardy and U.S. Pat. No. 5,356,425 to Bardy et al., which are incorporated herein by reference, describe a stimulator for applying stimulus pulses to the AV nodal fat pad in response to the heart rate exceeding a predetermined rate, in order to reduce the ventricular rate. The device also includes a cardiac pacemaker which serves to pace the ventricle in the event that the ventricular rate is lowered below a pacing rate, and provides for feedback control of the stimulus parameters applied to the AV nodal fat pad, as a function of the determined effect of the stimulus pulses on the heart rate.

U.S. Pat. No. 5,522,854 to Ideker et al., which is incorporated herein by reference, describes techniques for preventing arrhythmia by detecting a high risk of arrhythmia and then stimulating afferent nerves to prevent the arrhythmia.

U.S. Pat. No. 6,434,424 to Igel et al., which is incorporated herein by reference, describes a pacing system with a mode switching feature and ventricular rate regularization function adapted to stabilize or regularize ventricular heart rate during chronic or paroxysmal atrial tachyarrhythmia.

US Patent Application Publication 2002/0120304 to Mest, which is incorporated herein by reference, describes a method for regulating the heart rate of a patient by inserting into a blood vessel of the patient a catheter having an electrode at its distal end, and directing the catheter to an intravascular location so that the electrode is adjacent to a selected cardiac sympathetic or parasympathetic nerve.

U.S. Pat. Nos. 6,006,134 and 6,266,564 to Hill et al., which are incorporated herein by reference, describe an electro-stimulation device including a pair of electrodes for connection to at least one location in the body that affects or regulates the heartbeat.

PCT Publication WO 02/085448 to Foreman et al., which is incorporated herein by reference, describes a method for protecting cardiac function and reducing the impact of ischemia on the heart, by electrically stimulating a neural structure capable of carrying the predetermined electrical signal from the neural structure to the "intrinsic cardiac nervous system," which is defined and described therein.

U.S. Pat. No. 5,243,980 to Mehra, which is incorporated herein by reference, describes techniques for discrimination between ventricular and supraventricular tachycardia. In response to the detection of the occurrence of a tachycardia, stimulus pulses are delivered to one or both of the SA and AV nodal fat pads. The response of the heart rhythm to these stimulus pulses is monitored. Depending upon the change or lack of change in the heart rhythm, a diagnosis is made as to the origin of the tachycardia.

U.S. Pat. No. 5,658,318 to Stroetmann et al., which is incorporated herein by reference, describes a device for detecting a state of imminent cardiac arrhythmia in response to activity in nerve signals conveying information from the autonomic nerve system to the heart. The device comprises a sensor adapted to be placed in an extracardiac position and to detect activity in at least one of the sympathetic and vagus nerves.

U.S. Pat. No. 6,292,695 to Webster, Jr. et al., which is incorporated herein by reference, describes a method for controlling cardiac fibrillation, tachycardia, or cardiac arrhythmia by the use of a catheter comprising a stimulating electrode, which is placed at an intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

U.S. Pat. No. 6,134,470 to Hartlaub, which is incorporated herein by reference, describes an implantable anti-arrhythmia system which includes a spinal cord stimulator coupled to an implantable heart rhythm monitor. The monitor is adapted to detect the occurrence of tachyarrhythmias or of precursors thereto and, in response, trigger the operation of the spinal cord stimulator in order to prevent occurrences of tachyarrhythmias and/or as a stand-alone therapy for termination of tachyarrhythmias and/or to reduce the level of aggressiveness required of an additional therapy such as antitachycardia pacing, cardioversion or defibrillation.

A number of patents and articles describe other methods and devices for stimulating nerves to achieve a desired effect. Often these techniques include a design for an electrode or electrode cuff.

US Patent Publication 2003/0050677 to Gross et al., which is assigned to the assignee of the present patent application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

U.S. Pat. No. 4,608,985 to Crish et al. and U.S. Pat. No. 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode. The current applied to the electrodes blocks nerve transmission, but, as described, does not activate the nerve fibers in either direction.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33 (6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Manfredi M, "Differential block of conduction of larger fibers in peripheral nerve by direct current," Arch. Ital. Biol., 108:52-71 (1970)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$$\nabla(\sigma \nabla U) = 4\pi j,$$

where U is the potential, σ is the conductance tensor specifying the conductance of the various materials (electrode housing, axon, intracellular fluid, etc.), and j is a scalar function representing the current source density specifying the locations of current injection.

SUMMARY OF THE INVENTION

In some embodiments of the present invention, apparatus for treating a patient suffering from atrial fibrillation (AF) comprises a control unit and an electrode device, which is applied to a portion of a vagus nerve that innervates the heart of the patient. The control unit drives the electrode device to apply signals to the vagus nerve, and configures the signals to maintain pre-existing AF, i.e., to prevent the return to normal sinus rhythm (NSR). Typically, such pre-existing AF occurred spontaneously in the patient as a disease state, and was not artificially induced (e.g., for treating another heart condition). Alternatively or additionally, AF maintenance is achieved by electrical stimulation of cardiac tissue, such as fat pads, atrial tissue, or pulmonary veins, and/or by administering a drug.

In some embodiments of the present invention, AF is maintained long-term, e.g., longer than about three weeks. Such AF maintenance generally reduces the frequency of recurring transitions between AF and NSR, which transitions are common in patients with AF, particularly in patients with chronic episodic AF. Such repeated transitions are generally undesirable because: (a) they often cause discomfort for the patient, (b) they may increase the risk of thromboembolic events, and (c) they often make prescribing an appropriate drug regimen difficult. Drug regimens that are beneficial for the patient when in AF are often inappropriate when the patient is in NSR, and vice versa. Knowledge that the patient will generally remain in AF typically helps a physician prescribe a more appropriate and/or lower-dosage drug regimen.

In other embodiments of the present invention, AF is maintained short-term, typically between about one day and about three weeks. Such maintenance is generally beneficial during a period in which conventional anticoagulation drug therapy is applied to the patient prior to attempting electrical or pharmacological cardioversion. (Such a period may be desirable when an initial diagnosis of AF occurs more than 48 hours after initiation of AF, or an unknown amount of time after initiation of AF.) Cardioversion is generally not attempted during this period because of the particularly elevated risk of thromboembolic events before the anticoagulation therapy has had time to be effective. AF maintenance to prevent naturally-occurring cardioversion, i.e., reversion to NSR, during this period is believed by the inventors to reduce the risk of thromboembolic events in some patients.

In some embodiments of the present invention, the control unit drives the electrode device to apply signals to the vagus nerve, and configures the signals so as to increase atrial motion. Such increased atrial motion typically causes mixing of the blood in the atrium, which is believed by the inventors to reduce the likelihood of coagulation and resultant thromboembolic events in some patients. Alternatively or additionally, atrial motion is achieved by electrical stimulation of cardiac tissue, such as atrial tissue or fat pads. For some applications, atrial motion is increased using the techniques described herein upon the termination of AF, for example, to prevent or treat electro-mechanical-dissociation (EMD), in which cardiac electrical activity is not coupled with appropriate mechanical contraction.

In other embodiments of the present invention, the control unit drives the electrode device to apply signals to the vagus nerve, and configures the signals so as to restore NSR, i.e., to induce cardioversion. According to a first approach for restoring NSR, the configuration includes repeatedly changing parameters of the stimulation. Such switching of the stimulation in some instances causes fluctuations in the atrial effective refractory period (AERP), thereby breaking reentry cycles and restoring synchronization and NSR. According to a second approach, the control unit (a) paces the heart using conventional pacing techniques, such as by driving a conventional pacemaker to apply pacing signals to the heart, e.g., to the right atrium, right ventricle, or both ventricles, and, simultaneously, (b) configures the signals applied to the vagus nerve to provide generally constant vagal stimulation with a high intensity. The control unit then suddenly ceases vagal stimulation. Such sudden cessation generally destabilizes the atrial cells, resulting in a return to NSR. According to a third approach, typically appropriate for treating AF principally caused by heightened adrenergic tone, the control unit drives the electrode device to apply signals to the vagus nerve, and configures the signals to apply generally constant vagal stimulation, so as to restore NSR.

In some embodiments of the present invention, the apparatus is adapted to be used during conventional electrical atrial defibrillation. The control unit drives the electrode device to apply stimulating signals to the vagus nerve, and configures the stimulating signals to cause severe bradycardia during the defibrillation. Such severe bradycardia generally causes the patient to partially lose consciousness and thereby experience less pain during the defibrillation. The device thus can be thought of as a vagus nerve facilitated tranquilizer. For some applications, the control unit additionally and at generally the same time applies inhibiting signals to the vagus nerve, and configures the inhibiting signals to block vagal pain afferents, thereby further reducing pain experienced by the patient during the defibrillation. In some embodiments, a conventional pacemaker is applied to the heart, and is used to pace the heart in the event of excessive bradycardia caused by the vagal stimulation.

In some embodiments of the present invention, the apparatus comprises a timer and a sensor for detecting AF. When AF is detected, the timer begins a countdown, typically having a duration of between about 24 and 54 hours, such as 48 hours. The apparatus attempts to restore NSR during the countdown, using the cardioversion techniques and apparatus described herein, or methods and apparatus known in the art, such as an implantable defibrillator. Upon completion of the countdown, if NSR has not been successfully restored, the apparatus attempts to maintain AF, typically using techniques described herein. This AF maintenance typically continues until a physician intervenes by signaling the apparatus to terminate maintenance.

In some embodiments of the present invention, when applying the signal to the vagus nerve, the control unit drives the electrode device to (a) apply signals to induce the propagation of efferent action potentials towards the heart, and (b) suppress artificially-induced afferent action potentials towards the brain, in order to minimize any unintended side effect of the signal application. When inducing efferent action potentials towards the heart, the control unit typically drives the electrode device to selectively recruit nerve fibers beginning with smaller-diameter fibers, and to recruit progressively larger-diameter fibers as the desired stimulation level increases. Typically, in order to achieve this smaller-to-larger diameter fiber recruitment order, the control unit stimulates myelinated fibers essentially of all diameters using cathodic current from a central cathode, while simultaneously inhibiting fibers in a larger-to-smaller diameter order using anodal current ("efferent anodal current") from a set of one or more anodes placed between the central cathode and the edge of the electrode device closer to the heart ("the efferent anode set"). Thus, for example, if a small anodal current is applied, then action potentials induced by the cathodic current in the larger diameter fibers are inhibited (because the larger diameter fibers are sensitive to even a small anodal current), while action potentials induced by the cathodic current in smaller fibers are allowed to propagate towards the heart. The amount of parasympathetic stimulation delivered to the heart may generally be increased by decreasing the number of fibers affected by the efferent anodal current, in a smaller-to-larger diameter order, e.g., by decreasing the amplitude or frequency of the efferent anodal current applied to the nerve. Alternatively, the cathodic current is increased in order to increase the parasympathetic stimulation.

The control unit typically suppresses afferent action potentials induced by the cathodic current by inhibiting essentially all or a large fraction of fibers using anodal current ("afferent anodal current") from a second set of one or more anodes (the "afferent anode set"). The afferent anode set is typically placed between the central cathode and the edge of the electrode device closer to the brain (the "afferent edge"), to block a large fraction of fibers from conveying signals in the direction of the brain during application of the afferent anodal current.

In some embodiments of the present invention, the cathodic current is applied with an amplitude sufficient to induce action potentials in large- and medium-diameter fibers (e.g., A- and B-fibers), but insufficient to induce action potentials in small-diameter fibers (e.g., C-fibers). Simultaneously, an anodal current is applied in order to inhibit action potentials induced by the cathodic current in the large-diameter fibers (e.g., A-fibers), but not in the small- and medium-diameter fibers (e.g., B- and C-fibers). This combination of cathodic and anodal current generally results in the stimulation of medium-diameter fibers (e.g., B-fibers) only. At the same time, a portion of the afferent action potentials induced by the cathodic current are blocked, as described above. By not stimulating large-diameter fibers, such stimulation generally avoids adverse effects sometimes associated with recruitment of such large fibers, such as dyspnea and hoarseness. Stimulation of small-diameter fibers is avoided because these fibers transmit pain sensations and are important for regulation of reflexes such as respiratory reflexes.

In some embodiments of the present invention, the efferent anode set comprises a plurality of anodes. Application of the efferent anodal current in appropriate ratios from the plurality of anodes in these embodiments generally minimizes the "virtual cathode effect," whereby application of too large an anodal current creates a virtual cathode, which stimulates rather than blocks fibers. When such techniques are not used, the virtual cathode effect generally hinders blocking of smaller-diameter fibers, because a relatively large anodal current is typically necessary to block such fibers, and this same large anodal current induces the virtual cathode effect. Likewise, the afferent anode set typically comprises a plurality of anodes in order to minimize the virtual cathode effect in the direction of the brain.

In some embodiments of the present invention, vagal stimulation is applied in a burst (i.e., a series of pulses). The application of the burst in each cardiac cycle typically commences after a variable delay after a trigger such as a detected R-wave, P-wave, or other feature of an ECG. For some applications, other parameters of the applied burst are also varied in real time. Such other parameters include amplitude, number of pulses per trigger (PPT), pulse duration, and pulse repetition interval (i.e., the interval between the leading edges of two consecutive pulses). For some applications, the delay and/or one or more of the other parameters are calculated in real time using a function, the inputs of which include one or more pre-programmed but updateable constants and one or more sensed parameters, such as the R-R interval between cardiac cycles and/or the P-R interval. Alternatively or additionally, a lookup table of parameters, such as delays and/or other parameters, is used to determine in real time the appropriate parameters for each application of pulses, based on the one or more sensed parameters, and/or based on a predetermined sequence stored in the lookup table. For example, in embodiments of the present invention in which the control unit configures signals applied to the vagus nerve so as to induce cardioversion, such a predetermined sequence may include delays of alternating longer and shorter durations.

The use of the vagal stimulation techniques described herein may also have the additional beneficial effect of preventing electrical remodeling.

"Vagus nerve," and derivatives thereof, as used in the specification and the claims, is to be understood to include portions of the left vagus nerve, the right vagus nerve, and branches of the vagus nerve such as the superior cardiac nerve, superior cardiac branch, and inferior cardiac branch. Similarly, stimulation of the vagus nerve is described herein by way of illustration and not limitation, and it is to be understood that stimulation of other autonomic nerves, including nerves in the epicardial fat pads, pulmonary veins, carotid artery, carotid sinus, vena cava vein, and/or internal jugular vein, for treatment of heart conditions or other conditions, is also included within the scope of the present invention.

There is therefore provided, in accordance with an embodiment of the present invention, apparatus for treating a subject suffering from spontaneous atrial fibrillation (AF), including:

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply an electrical current to the site, and configure the current to maintain the spontaneous AF for at least about 24 hours, so as to treat the subject.

In an embodiment, the site includes the vagus nerve, the electrode device is adapted to be coupled to the vagus nerve, the control unit is adapted to configure the current to include a stimulating current, which is capable of inducing action potentials in a first set and a second set of nerve fibers of the vagus nerve, and an-inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

In an embodiment, the site includes the vagus nerve, the electrode device is adapted to be coupled to the vagus nerve, the current includes a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve.

For some applications, the control unit is adapted to drive the electrode device to configure the current to maintain the AF for between about 24 hours and about three weeks. Alternatively, the control unit is adapted to drive the electrode device to configure the current to maintain the AF for at least about three weeks.

In an embodiment, the apparatus includes a sensor adapted to detect normal sinus rhythm (NSR) and generate a sensor signal responsive thereto, and the control unit is adapted to receive the sensor signal, and to drive the electrode device to apply the current responsive to the sensor signal.

In an embodiment, the apparatus includes a sensor adapted to detect the AF and generate a sensor signal responsive thereto, and the control unit is adapted to receive the sensor signal, and to drive the electrode device to apply the current responsive to the sensor signal.

In an embodiment, the apparatus including a cardiac electrode device, adapted to be coupled to cardiac tissue of the subject, and the control unit is adapted to:

drive the cardiac electrode device to apply a cardiac electrical current to the cardiac tissue, and configure the cardiac electrical current to maintain the spontaneous AF, so as to treat the subject.

For some applications, the control unit is adapted to drive the electrode device to apply the current with an amplitude of between about 2 and about 5 milliamps.

In an embodiment, the control unit is adapted to drive the electrode device to apply the current in respective bursts in each of a plurality of cardiac cycles of the subject. For some applications, the control unit is adapted to configure each pulse of each of the bursts to have a pulse duration of between about 1 and about 3 milliseconds. For some applications, the control unit is adapted to configure each burst to have between about 1 and about 8 pulses. For some applications, the control unit is adapted to configure each pulse of each of the bursts to have a pulse duration of between about 0.5 and about 3 milliseconds. For some applications, the control unit is adapted to configure each of the bursts to contain between about 1 and about 100 pulses.

For some applications, the apparatus includes a sensor adapted to detect a complex in a cardiac rhythm of the subject, and generate a sensor signal responsive thereto, and the control unit is adapted to receive the sensor signal, and to drive the electrode device to apply the current responsive to the sensor signal.

There is also provided, in accordance with an embodiment of the present invention, apparatus for treating a subject suffering from spontaneous atrial fibrillation (AF), including:

an electrode device, adapted to be coupled to tissue of the subject; and a control unit, adapted to:

drive the electrode device to apply an electrical current to the tissue, and configure the current to maintain the spontaneous AF for at least about 24 hours, so as to treat the subject.

For some applications, the control unit is adapted to configure the current to maintain the AF for between about 24 hours and about three weeks. Alternatively, the control unit is adapted to configure the current to maintain the AF for at least about three weeks.

In an embodiment, the apparatus includes a sensor adapted to detect normal sinus rhythm (NSR) and generate a sensor signal responsive thereto, and the control unit is adapted to receive the sensor signal, and to drive the electrode device to apply the current responsive to the sensor signal.

In an embodiment, the apparatus includes a sensor adapted to detect the AF and generate a sensor signal responsive thereto, and the control unit is adapted to receive the sensor signal, and to drive the electrode device to apply the current responsive to the sensor signal.

For some applications, the control unit is adapted to drive the electrode device to apply the current at a frequency of at least about 3 Hz.

In an embodiment, the tissue includes cardiac tissue of the subject, and the electrode device is adapted to be coupled to the cardiac tissue. In an embodiment, the tissue is selected from the list consisting of: atrial tissue, cardiac fat pad tissue, a pulmonary vein, a carotid artery, a carotid sinus, a vena cava vein, and an internal jugular vein, and the electrode device is adapted to be coupled to the selected tissue.

There is further provided, in accordance with an embodiment of the present invention, treatment apparatus, including:

an electrode device, adapted to be coupled to tissue of a subject; and a control unit, adapted to:

drive the electrode device to apply an electrical current to the tissue, and configure the current to modify atrial motion of the subject to a level sufficient to reduce a risk of an occurrence of a thromboembolic event.

In an embodiment, the control unit is adapted to configure the current to modify blood flow within an atrium of the subject.

In an embodiment, the electrode device is adapted to be coupled to the tissue of the subject, the subject suffering from atrial fibrillation (AF) or from increased risk of thromboembolic events.

In an embodiment, the control unit is adapted to configure the current to increase blood flow out of a left atrial auricle of the subject.

In an embodiment, the apparatus includes a sensor adapted to detect an occurrence of atrial fibrillation (AF) and generate a sensor signal responsive thereto, and the control unit is adapted to receive the sensor signal, and to drive the electrode device to apply the current during the occurrence of the AF.

In an embodiment, the apparatus includes a sensor adapted to detect an occurrence of atrial fibrillation (AF) and generate a sensor signal responsive thereto, and the control unit is adapted to drive the electrode device to apply the current in the absence of the occurrence of the AF.

In an embodiment, the tissue includes cardiac tissue of the subject, and the electrode device is adapted to be coupled to the cardiac tissue. In an embodiment, the tissue is selected from the list consisting of: atrial tissue, cardiac fat pad tissue, a pulmonary vein, a carotid artery, a carotid sinus, a vena cava vein, and an internal jugular vein, and the electrode device is adapted to be coupled to the selected tissue.

In an embodiment, the tissue includes a vagus nerve of the subject, and the electrode device is adapted to be coupled to the vagus nerve. In an embodiment, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

In an embodiment, the control unit is adapted to configure the current to include a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve.

In an embodiment, the control unit is adapted to:
during a first stimulation period, configure the current to cause a reduction in a force of contraction of atrial cells of the subject, and
during a second stimulation period, configure the current to cause an increase in the reduced force of contraction of the atrial cells.

For some applications, the control unit is adapted to set the first stimulation period to have a duration of between about 100 milliseconds and about 1000 milliseconds. Alternatively, the control unit is adapted to set the second stimulation period to have a duration of between about 200 milliseconds and about 15 seconds. For some applications, the control unit is adapted to configure the current to have a first frequency during the first stimulation period, and a second frequency during the second stimulation period, the first frequency greater than the second frequency.

For some applications, the control unit is adapted to configure the current to have a first amplitude during the first stimulation period, and a second amplitude during the second stimulation period, the first amplitude greater than the second amplitude.

In an embodiment, the control unit is adapted to:
drive the electrode device to apply the current during the first stimulation period, and
withhold the electrode device from applying the current during the second stimulation period.

In an embodiment, the control unit is adapted to:
during the first stimulation period, configure the current so as to induce action potentials in the vagus nerve, and
during the second stimulation period, configure the current so as to block action potentials in the vagus nerve.

In an embodiment, the control unit is adapted to configure the current so as to induce action potentials in the vagus nerve during the first and the second stimulation periods.

In an embodiment, the control unit is adapted to:
drive the electrode device to apply the current in respective bursts in each of a plurality of cardiac cycles of the subject, and
configure each pulse of each of the bursts to have a pulse width of at least a first pulse width during the first stimulation period, and to have a pulse width of less than a second pulse width during the second stimulation period, the first pulse width being greater than or equal to the second pulse width.

In an embodiment, the control unit is adapted to:
drive the electrode device to apply the current in respective bursts in each of a plurality of cardiac cycles of the subject, and
configure each of the bursts to have a number of pulses of at least a first number of pulses during the first stimulation period, and to have a number of pulses of less than a second number of pulses during the second stimulation period, the first number of pulses being greater than or equal to the second number of pulses.

In an embodiment, the apparatus includes a sensor, adapted to sense at least one physiological variable of the subject, and to generate a sensor signal responsive thereto, and the control unit is adapted to receive the sensor signal and to synchronize therewith a commencement of at least one of the first and second stimulation periods. For some applications, the sensed physiological variable includes a QRS-complex of the subject, and the control unit is adapted to initiate the first stimulation period within about 50 milliseconds after an occurrence of the QRS-complex. Alternatively or additionally, the sensed physiological variable includes an expiration by the subject, and the control unit is adapted to initiate the first stimulation period within about 500 milliseconds after a beginning of the expiration. Further alternatively or additionally, the sensed physiological variable includes diastole of the subject, and the control unit is adapted to initiate the second stimulation period substantially simultaneously with a portion of the diastole.

There is still further provided, in accordance with an embodiment of the present invention, treatment apparatus, including:
an electrode device, adapted to be coupled to a site of a subject suffering from atrial fibrillation (AF), the site selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and
a control unit, adapted to:
drive the electrode device to apply an electrical current to the site, and
repeatedly change at least one parameter of the current, so as to restore normal sinus rhythm (NSR) of the subject.

In an embodiment, the site includes the vagus nerve, the electrode device is adapted to be coupled to the vagus nerve, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

In an embodiment, the control unit is adapted to configure the current to include a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve. For some applications, the parameter includes an amplitude of the current, and the control unit is adapted to repeatedly change the amplitude. Alternatively or additionally, the parameter includes a frequency of the current, and the control unit is adapted to repeatedly change the frequency.

In an embodiment, the control unit is adapted to drive the electrode device to apply the current in respective bursts in each of a plurality of cardiac cycles of the subject, the parameter includes a number of pulses in each of the bursts, and the control unit is adapted to repeatedly change the number of pulses in each of the bursts.

In an embodiment, the control unit is adapted to drive the electrode device to apply the current in respective bursts in each of a plurality of cardiac cycles of the subject, the parameter includes a pulse width of pulses in each of the bursts, and the control unit is adapted to repeatedly change the pulse width of the pulses in each of the bursts.

In an embodiment, the control unit is adapted to drive the electrode device to apply the electrical current in pulses, the parameter includes a pulse width of the pulses, and the control unit is adapted to repeatedly change the pulse width.

In an embodiment, the parameter includes an on/off status of the current, and the control unit is adapted to repeatedly change the on/off status. For some applications, the control unit is adapted to repeatedly change a duration of at least one period selected from the list consisting of: an "on" period of the current, and an "off" period of the current.

In an embodiment, the control unit is adapted to:

during a first period, configure the current so as to induce action potentials in the site, and during a second period, configure the current so as to block action potentials in the site.

In an embodiment, the control unit is adapted to repeatedly change the parameter at a rate of between about one change per heart beat of the subject and about one change per 30 seconds.

In an embodiment, the control unit is adapted to repeatedly change the parameter according to a predetermined patter. Alternatively or additionally, the control unit is adapted to repeatedly change the parameter randomly. For some applications, the control unit is adapted to repeatedly change the parameter randomly, with an interval between each change of between about 500 milliseconds and about 30 seconds.

In an embodiment, the apparatus includes a sensor, adapted to detect an occurrence of the AF and generate a sensor signal indicative thereof and the control unit is adapted to receive the sensor signal, and to drive the electrode device to apply the current responsive to the sensor signal.

There is additionally provided, in accordance with an embodiment of the present invention, treatment apparatus, including:

an electrode device, adapted to be coupled to a site of a subject suffering from atrial fibrillation (AF), the site selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

a pacing device, adapted to be applied to a heart of the subject; and a control unit, adapted to:

during a first period, drive the pacing device to pace the heart, and drive the electrode device to apply an electrical current to the site, and during a second period following the first period, withhold the electrode device from applying the electrical current to the site.

In an embodiment, the control unit is adapted to configure a parameter of at least one of the periods to be such as to restore normal sinus rhythm (NSR) of the subject within 2 hours after initiation of the second period.

In an embodiment, the site includes the vagus nerve, the electrode device is adapted to be coupled to the vagus nerve, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

In an embodiment, the site includes the vagus nerve, the electrode device is adapted to be coupled to the vagus nerve, the control unit is adapted to configure the current to include a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve.

In an embodiment, the control unit is adapted to withhold the pacing device from pacing the heart during at least a portion of the second period.

In an embodiment, the control unit is adapted to configure the first period to have a duration of between about 500 milliseconds and about 30 seconds.

In an embodiment, the control unit is adapted to drive the electrode device to apply the electrical current substantially without changing the parameter during the first period, and with an amplitude greater than about 6 milliamps.

In an embodiment, the apparatus includes a sensor, adapted to detect an occurrence of the AF and generate a sensor signal indicative thereof, and the control unit is adapted to receive the sensor signal, and to drive the pacing device and drive the electrode device to apply the electrical current responsive to the sensor signal.

In an embodiment, the apparatus includes a sensor, adapted to detect an occurrence of the AF and generate a sensor signal indicative thereof, and the control unit is adapted to receive the sensor signal, and to withhold the electrode device from applying the electrical current responsive to the sensor signal.

In an embodiment, the control unit is adapted to configure the pacing device to pace the heart by applying a pacing signal to the heart having a pulse repetition interval having a duration of between about 50% and about 200% of an atrial refractory period of the subject.

In an embodiment, the control unit is adapted to configure the current to modulate an atrial refractory period of the subject.

In an embodiment, the control unit is adapted to configure a parameter of the current selected from the list consisting of: an on/off time of the current, an amplitude of the current, a number of pulses of the current, a pulse repetition interval of the current, a frequency of pulses within a pulse burst of the current, a pulse width of pulses of the current, pulses per trigger of the current, a duty cycle of the current, and timing of the current within a cardiac cycle of the subject.

In an embodiment, the control unit is adapted to configure a parameter of the pacing selected from the list consisting of: an on/off time of the pacing, an amplitude of the pacing, a number of pulses of the pacing, a pulse repetition interval of the pacing, a frequency of pulses within a pulse burst of the pacing, a pulse width of pulses of the pacing, pulses per trigger of the pacing, a duty cycle of the pacing, and timing of the pacing within a cardiac cycle of the subject.

There is yet additionally provided, in accordance with an embodiment of the present invention, treatment apparatus, including:

an electrode device, adapted to be coupled to a site of a subject suffering from atrial fibrillation (AF), the site selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

a pacing device, adapted to be applied to a heart of the subject;

a sensor, adapted to detect an occurrence of the AF and generate a sensor signal indicative thereof, and a control unit, adapted to:

during a first period, drive the pacing device to pace the heart, and drive the electrode device to apply an electrical current to the site, and responsive to the sensor signal, during a second period following the first period, withhold the electrode device from applying the electrical current to the site.

In an embodiment, the site includes the vagus nerve, the electrode device is adapted to be coupled to the vagus nerve, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

In an embodiment, the site includes the vagus nerve, the electrode device is adapted to be coupled to the vagus nerve, the control unit is adapted to configure the current to include a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve.

In an embodiment, the control unit is adapted to, during the first period, drive the pacing device and drive the electrode device to apply the current responsive to the sensor signal.

In an embodiment, the control unit is adapted to withhold the pacing device from pacing the heart during at least a portion of the second period.

In an embodiment, the control unit is adapted to drive the electrode device to apply the electrical current substantially without changing a parameter of the current during the first period, and with an amplitude greater than about 6 milliamps.

In an embodiment, the control unit is adapted to withhold the electrode device from applying the electrical current during the second period responsive to an indication in the sensor signal of a P-wave of the subject.

In an embodiment, the sensor is adapted to generate the sensor signal responsive to a measure of at least one ventricular response parameter, the parameter selected from the list consisting of: a ventricular response rate and a ventricular response variability.

In an embodiment, the sensor is adapted to generate the sensor signal responsive to a measure of pressure, selected from the list consisting of: atrial pressure, venous pressure, and arterial pressure.

In an embodiment, the sensor signal includes a first sensor signal and a second sensor signal, the first sensor signal includes a measure of pressure, selected from the list consisting of: atrial pressure, venous pressure, and arterial pressure, the second sensor signal includes an indication of ventricular contraction, the sensor is adapted to generate the first and the second sensor signals, and the control unit is adapted to receive the first and the second sensor signals, and to detect the AF by analyzing at least one relationship between the first and the second sensor signals.

In an embodiment, the sensor signal includes an electrocardiogram (ECG) signal, the sensor is adapted to measure the ECG signal, and the control unit is adapted to receive the ECG signal, and to detect the AF by analyzing a duration of an isoelectrical segment of the ECG signal.

There is also provided, in accordance with an embodiment of the present invention, treatment apparatus, including:

an electrode device, adapted to be coupled to a site of a subject suffering from atrial fibrillation (AF) principally caused by heightened adrenergic tone, the site selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to drive the electrode device to apply to the site an electrical stimulating current, which current is capable of inducing action potentials in the site, the current configured to be such as to restore normal sinus rhythm (NSR) of the subject.

In an embodiment, the control unit is adapted to drive the electrode device to apply the current, substantially without changing a parameter of the current.

In an embodiment, the site includes the vagus nerve, the electrode device is adapted to be coupled to the vagus nerve, the control unit is adapted to configure the stimulating current so as to induce action potentials in a first set and a second set of nerve fibers of the vagus nerve, and the control unit is adapted to drive the electrode device to apply to the vagus nerve an inhibiting current, which is capable of inhibiting the induced action potentials traveling in the second set of nerve fibers, the nerve fibers in the second set having generally larger diameters than the nerve fibers in the first set.

In an embodiment, the site includes the vagus nerve, the electrode device is adapted to be coupled to the vagus nerve, the control unit is adapted to drive the electrode device to apply to the vagus nerve an inhibiting current, which is capable of inhibiting device-induced action potentials traveling in the vagus nerve in an afferent direction towards a brain of the subject.

In an embodiment, the apparatus includes a sensor, adapted to detect an occurrence of the AF and generate a sensor signal indicative thereof, and the control unit is adapted to receive the sensor signal, and to drive the electrode device to apply the stimulating current responsive to the sensor signal.

In an embodiment, the control unit is adapted to apply the stimulating current in respective bursts in each of a plurality of cardiac cycles of the subject, each pulse of each of the bursts having a pulse width of between about 0.5 milliseconds and about 1.5 milliseconds.

In an embodiment, the control unit is adapted to apply the stimulating current in respective bursts in each of a plurality of cardiac cycles of the subject, each of the bursts having between about 1 and about 10 pulses.

In an embodiment, the control unit is adapted to apply the stimulating current in respective bursts synchronized with a cardiac cycle of the subject. for some applications, the control unit is adapted to apply a first pulse of each of the bursts after a delay from a sensed feature of an electrocardiogram (ECG) of the subject. For some applications, the sensed feature is selected from the list consisting of: a P-wave of the ECG and an R-wave of the ECG, and the control unit is adapted to apply the first pulse after the delay from the selected sensed feature.

There is further provided, in accordance with an embodiment of the present invention, apparatus for use during defibrillation of a subject suffering from atrial fibrillation (AF), including:

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply an electrical current to the site, and configure the current to cause bradycardia and a decreased level of alertness during the defibrillation.

In an embodiment, the site includes the vagus nerve, the electrode device is adapted to be coupled to the vagus nerve, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve.

In an embodiment, the site includes the vagus nerve, the electrode device is adapted to be coupled to the vagus nerve, the control unit is adapted to configure the current to include a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve.

In an embodiment, the site includes the vagus nerve, the electrode device is adapted to be coupled to the vagus nerve, and the control unit is adapted to:

apply an inhibiting electrical signal to the vagus nerve, and configure the inhibiting signal to block action potentials traveling in the vagus nerve in an afferent direction toward a brain of the subject.

In an embodiment, the apparatus includes a pacing device, adapted to be applied to a heart of the subject, and the control unit is adapted to drive the pacing device to pace the heart if a heart rate of the subject falls below a predetermined rate responsive to application of the current configured to cause the decreased level of alertness.

In an embodiment, the control unit is adapted to drive the electrode device to apply the current with an amplitude of between about 4 and about 8 milliamps.

In an embodiment, the control unit is adapted to drive the electrode device to apply the current in respective bursts in each of a plurality of cardiac cycles of the subject For some applications, the control unit is adapted to configure each pulse of each of the bursts to have a pulse duration of between about 1 and about 3 milliseconds. For some applications, the control unit is adapted to configure each burst to have between about 6 and about 10 pulses.

There is still further provided, in accordance with an embodiment of the present invention, apparatus for treating a subject suffering from atrial fibrillation (AF), including:

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

a sensor, adapted to be applied to tissue of the subject, and to generate at least one sensor signal responsive to a sensed physiological parameter of the subject; and a control unit, adapted to:

detect the AF by receiving and analyzing the at least one sensor signal, responsive to detecting the AF, drive the electrode device to apply an electrical current to the site, during a first period beginning upon detecting the AF, configure the current to attempt to restore normal sinus rhythm (NSR) of the subject, determine whether NSR has been restored, and during a second period beginning responsive to determining that NSR has not been restored within a threshold period of time after detecting the AF, configure the current to maintain AF.

In an embodiment, the site includes the vagus nerve, the electrode device is adapted to be coupled to the vagus nerve, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set, and the control unit is adapted to drive the electrode device to apply the stimulating current and the inhibiting current to the vagus nerve, responsive to detecting the AF.

In an embodiment, the site includes the vagus nerve, the electrode device is adapted to be coupled to the vagus nerve, the control unit is adapted to configure the current to include a stimulating current, which is capable of inducing action potentials in the vagus nerve, and an inhibiting current, which is capable of inhibiting device-induced action potentials traveling in the vagus nerve in an afferent direction toward a brain of the subject, and the control unit is adapted to drive the electrode device to apply the stimulating current and the inhibiting current to the vagus nerve, responsive to detecting the AF.

In an embodiment, the sensed physiological parameter includes a P-wave of the subject, and the sensor is adapted to generate the sensor signal responsive to the P-wave. Alternatively or additionally, the sensed physiological parameter includes a measure of at least one ventricular response parameter of the subject, the parameter selected from the list consisting of: a ventricular response rate and a ventricular response variability, and the sensor is adapted to generate the sensor signal responsive to the ventricular response parameter. Further alternatively or additionally, the sensed physiological parameter includes a measure of pressure of the subject, selected from the list consisting of: atrial pressure, venous pressure, and arterial pressure, and the sensor is adapted to generate the sensor signal responsive to the measure of the pressure.

In an embodiment, the sensed physiological parameter includes a first sensed physiological parameter and a second sensed physiological parameter, the first sensed physiological parameter includes a measure of pressure of the subject, selected from the list consisting of: atrial pressure, venous pressure, and arterial pressure, the second sensed physiological parameter includes an indication of ventricular contraction of the subject, the sensor is adapted to generate a first sensor signal and a second sensor signal responsive to the measure of pressure and the indication of ventricular contraction, respectively, and the control unit is adapted to receive the first and the second sensor signals, and to detect the AF by analyzing at least one relationship between the first and the second sensor signals.

In an embodiment, the sensed physiological parameter includes an electrocardiogram (ECG) signal of the subject, the sensor is adapted to generate the sensor signal responsive to the ECG signal, and the control unit is adapted to receive the sensor signal, and to detect the AF by analyzing a duration of an isoelectrical segment of the ECG signal.

In an embodiment, the control unit is adapted to configure the current to attempt to restore NSR by repeatedly changing at least one parameter of the current.

In an embodiment, the apparatus includes a pacing device, adapted to be applied to a heart of the subject, and the control unit is adapted to attempt to restore NSR during the first period by:

during a pacing period within the first period, driving the pacing device to pace the heart, and driving the electrode device to apply the current to the site, and during a withholding period following the pacing period, withholding the electrode device from applying the current to the site.

For some applications, the control unit is adapted to configure the pacing device to i pace the heart by applying a pacing signal to the heart having a pulse repetition interval having a duration of between about 50% and about 200% of an atrial refractory period of the subject.

For some applications, the control unit is adapted to configure the current to modulate an atrial refractory period of the subject.

For some applications, the control unit is adapted to configure a parameter of the current selected from the list consisting of: an on/off time of the current, an amplitude of the current, a number of pulses of the current, a pulse repetition interval of the current, a frequency of pulses within a pulse burst of the current, a pulse width of pulses of the current, pulses per trigger of the current, a duty cycle of the current, and timing of the current within a cardiac cycle of the subject.

For some applications, the control unit is adapted to configure a parameter of the pacing selected from the list consisting of: an on/off time of the pacing, an amplitude of the pacing, a number of pulses of the pacing, a pulse repetition interval of the pacing, a frequency of pulses within a pulse burst of the pacing, a pulse width of pulses of the pacing, pulses per trigger of the pacing, a duty cycle of the pacing, and timing of the pacing within a cardiac cycle of the subject.

In an embodiment, the control unit is adapted to generate a notification signal upon determining that NSR has been restored.

In an embodiment, the control unit is adapted to maintain a duration of the threshold period between about 24 and 54 hours. For some applications, the control unit is adapted to maintain a duration of the threshold period between about 44 and 52 hours.

In an embodiment, the control unit is adapted to record a time of detecting of the AF. For some applications, the control unit is adapted to output the recorded time upon interrogation by a user.

There is additionally provided, in accordance with an embodiment of the present invention, apparatus for nerve stimulation, including an electrode device, adapted to be coupled to a nerve of a subject, the nerve including a first set of fibers situated in a vicinity of an external surface of the nerve, and a second set of fibers situated in a vicinity of a longitudinal axis of the nerve, and adapted to generate an electrical field defining a first activation function at the first set of fibers, and defining a second activation function at the second set of fibers, the first activation function being less than about four times greater than the second activation function.

In an embodiment, the electrode device is adapted to be fixed to the nerve.

In an embodiment, the electrode device includes one or more electrodes having respective conductive surfaces, which are adapted to be coupled to the nerve such that a distance between each of the conductive surfaces and the axis of the nerve is at least about 0.5 millimeters.

In an embodiment, the nerve includes a vagus nerve of the subject, and the electrode device is adapted to be coupled to the vagus nerve.

In an embodiment, the electrode device is adapted to generate the electrical field by applying a current having an amplitude of at least 5 milliamps. For some applications, the electrode device is adapted to generate the electrical field by applying the current having an amplitude of at least 7 milliamps.

There is yet additionally provided, in accordance with an embodiment of the present invention, apparatus for nerve stimulation, including:

one or more electrodes having respective conductive surfaces, which are adapted to be coupled to a nerve of a subject such that a distance between each of the conductive surfaces and an axis of the nerve is at least about 0.5 millimeters; and a control unit, adapted to drive the electrodes to apply a current having an amplitude of at least 5 milliamps.

In an embodiment, the apparatus includes one or more insulating elements that separate the electrodes from one another, such that a distance between each of the insulating elements and the axis of the nerve is between about 0.5 and about 3 millimeters.

In an embodiment, the control unit is adapted to drive the electrodes to apply the current having an amplitude of at least 7 milliamps.

In an embodiment, the nerve includes a vagus nerve of the subject, and the electrodes are adapted to be coupled to the vagus nerve.

In an embodiment, the electrodes are adapted to be coupled to the nerve such that the distance between each of the conductive surfaces and the axis of the nerve is at least about 1.5 millimeters.

In an embodiment, the electrodes are adapted to be coupled to the nerve such that the distance between each of the conductive surfaces and the axis of the nerve is less than about 2 millimeters.

In an embodiment, the electrodes are adapted to be coupled to the nerve such that the distance between each of the conductive surfaces and the axis of the nerve is at least about 3 millimeters.

There is also provided, in accordance with an embodiment of the present invention, apparatus for stimulating a nerve of a subject, the nerve including small-, medium-, and large-diameter fibers, the apparatus including:

a cathode, adapted to be disposed at a cathodic site of the nerve, and to apply a cathodic current to the nerve which is capable of inducing action potentials in the nerve;

an anode, adapted to be disposed at an anodal site of the nerve, and to apply to the nerve an anodal current which is capable of inhibiting action potentials in the nerve; and a control unit, adapted to:

drive the cathode to apply to the nerve the cathodic current having a cathodic amplitude sufficient to induce action potentials in the medium- and large-diameter fibers, but generally insufficient to induce action potentials in the small-diameter fibers, and simultaneously drive the anode to apply to the nerve the anodal current having an anodal amplitude sufficient to inhibit action potentials in the large-diameter fibers, but generally insufficient to inhibit action potentials in the medium-diameter fibers.

In an embodiment, the nerve includes a vagus nerve of the subject, the cathode is adapted to be disposed at the cathodic site of the vagus nerve, and the anode is adapted to be disposed at the anodal site of the vagus nerve.

In an embodiment, the nerve includes a first set of fibers situated in a vicinity of an external surface of the nerve, and a second set of fibers situated in a vicinity of a longitudinal axis of the nerve, and the cathode is adapted to generate an electrical field defining a first activation function at the first set of fibers, and defining a second activation function at the second set of fibers, the first activation function less than about four times greater than the second activation function.

For some applications, the control unit is adapted to set the cathodic amplitude to be between about 1 and about 10 milliamps. For some applications, according to claim 128, the control unit is adapted to set the anodal amplitude to be between about 1 and about 10 milliamps.

In an embodiment, the apparatus includes a suppression anode, adapted to:

be disposed at a suppression anodal site of the nerve so that the cathodic site is between the anodal site and the suppression anodal site, and apply to the nerve a suppression anodal current having a suppression anodal amplitude sufficient to inhibit action potentials induced in the nerve by the cathodic current and propagating in a direction from the cathodic site towards the suppression anodal site. For some applications, the suppression anode is adapted to apply the suppression anodal current with the suppression anodal amplitude sufficient to inhibit a portion of the action potentials induced in the nerve by the cathodic current and propagating towards the suppression anodal site.

There is further provided, in accordance with an embodiment of the present invention, apparatus, including:

an electrode device, adapted to be coupled to a nerve of a subject; and a control unit, adapted to:

drive the electrode device to apply to the nerve a stimulating current, which has a stimulating amplitude sufficient to induce action potentials in a first set and a second set of nerve fibers of the nerve, but not in a third set of nerve fibers of the nerve, the nerve fibers in the first set having generally larger diameters than the nerve fibers in the second set, and the nerve fibers in the second set having generally larger diameters than the nerve fibers in the third set, and drive the electrode device to apply to the nerve an inhibiting current, which has an inhibiting amplitude sufficient to inhibit the induced action potentials in the first set of nerve fibers, but not in the second set of nerve fibers.

In an embodiment, the nerve includes a vagus nerve of the subject, and the electrode device is adapted to be coupled to the vagus nerve.

In an embodiment, the control unit is adapted to:

drive the electrode device to apply the stimulating current, configured to induce the action potentials in an efferent therapeutic direction towards a heart of the subject, and drive the electrode device to apply the inhibiting current, configured to inhibit the induced action potentials traveling in the efferent therapeutic direction in the first set of nerve fibers.

In an embodiment, the control unit is adapted to:

drive the electrode device to apply the stimulating current, configured to induce the action potentials in an afferent therapeutic direction towards a brain of the subject, and drive the electrode device to apply the inhibiting current, configured to inhibit the induced action potentials traveling in the afferent therapeutic direction in the first set of nerve fibers.

In an embodiment, the nerve includes a surface set of fibers situated in a vicinity of an external surface of the nerve, and an axial set of fibers situated in a vicinity of a longitudinal axis of the nerve, and the control unit is adapted to drive the electrode device to apply the stimulating current to generate an electrical field defining a first activation function at the surface set of fibers, and defining a second activation function at the axial set of fibers, the first activation function less than about four times greater than the second activation function. For some applications, the control unit is adapted to configure the stimulating amplitude to be between about 1 and about 10 milliamps. For some applications, the control unit is adapted to configure the inhibiting amplitude to be between about 1 and about 10 milliamps.

There is still further provided, in accordance with an embodiment of the present invention, a treatment method, including:

applying an electrical current to a site of a subject identified as suffering from spontaneous atrial fibrillation (AF), the site selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject, and configuring the current to treat the subject by maintaining the spontaneous AF for at least about 24 hours.

There is additionally provided, in accordance with an embodiment of the present invention, a treatment method, including:

identifying a subject suffering from spontaneous atrial fibrillation (AF);

applying a treatment to the subject; and configuring the treatment to treat the subject by maintaining the spontaneous AF for at least about 24 hours.

There is yet additionally provided, in accordance with an embodiment of the present invention, a treatment method, including:

applying an electrical current to tissue of a subject; and configuring the current to modify atrial motion of the subject to a level sufficient to reduce a risk of an occurrence of a thromboembolic event.

There is also provided, in accordance with an embodiment of the present invention, a treatment method, including:

applying an electrical current to a site of a subject suffering from atrial fibrillation (AF), the site selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and repeatedly changing at least one parameter of the current, so as to restore normal sinus rhythm (NSR) of the subject.

There is further provided, in accordance with an embodiment of the present invention, a treatment method, including:

during a first period, pacing a heart of a subject suffering from atrial fibrillation (AF), and applying an electrical current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

during a second period following the first period, withholding applying the current to the site.

There is still further provided, in accordance with an embodiment of the present invention, a treatment method, including:

during a first period, pacing a heart of a subject suffering from atrial fibrillation (AF), and applying an electrical current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

detecting an occurrence of the AF; and responsive to detecting the AF, during a second period following the first period, withholding applying the current to the site.

There is additionally provided, in accordance with an embodiment of the present invention, a treatment method, including:

identifying a subject suffering from atrial fibrillation (AF) principally caused by heightened adrenergic tone;

applying, to a site of the subject, which is capable of inducing action potentials in the site, the site selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the stimulating current to restore normal sinus rhythm (NSR) of the subject.

There is yet additionally provided, in accordance with an embodiment of the present invention, a method for use during defibrillation of a subject suffering from atrial fibrillation (AF), including:

applying an electrical current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current to reduce pain experienced by the subject during the defibrillation, by causing bradycardia and a decreased level of alertness during the defibrillation.

There is also provided, in accordance with an embodiment of the present invention, a method for treating a subject suffering from atrial fibrillation (AF), including:

detecting the AF;

responsive to detecting the AF, applying an electrical current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

during a first period beginning upon detecting the AF, configuring the current to attempt to restore normal sinus rhythm (NSR) of the subject;

determining whether NSR has been restored; and during a second period beginning responsive to determining that NSR has not been restored within a threshold period of time after detecting the AF, configuring the current to maintain AF.

There is further provided, in accordance with an embodiment of the present invention, a method for stimulating a nerve of a subject, the nerve including a first set of fibers situated in a vicinity of an external surface of the nerve, and a second set of fibers situated in a vicinity of a longitudinal axis of the nerve, the method including applying to the nerve an electrical field defining a first activation function at the first set of fibers, and defining a second activation function at the second set of fibers, the first activation function less than about four times greater than the second activation function.

There is still further provided, in accordance with an embodiment of the present invention, a method for stimulating a nerve including small-, medium-, and large-diameter fibers, the method including:

applying a cathodic current to the nerve at a cathodic site of the nerve, so as to stimulate the nerve, the cathodic current having a cathodic amplitude sufficient to induce action potentials in the medium- and large-diameter fibers, but generally insufficient to induce action potentials in the small-diameter fibers; and simultaneously applying to the nerve, at an anodal site of the nerve, an anodal current, which is capable of inhibiting action potentials in the nerve, the anodal current having an anodal amplitude sufficient to inhibit action potentials in the large-diameter fibers, but generally insufficient to inhibit action potentials in the medium-diameter fibers.

There is additionally provided, in accordance with an embodiment of the present invention, a method for stimulating a nerve, including:

applying to the nerve a stimulating current, which has a stimulating amplitude sufficient to induce action potentials in a first set and a second set of nerve fibers of the nerve, but not in a third set of nerve fibers of the nerve, the nerve fibers in the first set having generally larger diameters than the nerve fibers in the second set, and the nerve fibers in the second set having generally larger diameters than the nerve fibers in the third set; and applying to the nerve an inhibiting current, which has an inhibiting amplitude sufficient to inhibit the induced action potentials in the first set of nerve fibers, but not in the second set of nerve fibers.

There is also provided, in accordance with an embodiment of the present invention, apparatus for treating a subject, including:

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply electrical stimulation to the site, and configure the stimulation to prevent an occurrence of atrial fibrillation (AF).

For some applications, the control unit is configured to substantially continuously drive the electrode device to apply the stimulation during an application period lasting at least about 3 weeks. For some applications, in an operating mode of the control unit, the control unit is adapted to drive the electrode device to apply the stimulation during an application period lasting at least about 3 weeks, and to configure the stimulation such that, during the application period, a longest duration of time in which no stimulation is applied is less than 4 hours.

For some applications, the apparatus includes a sensor, adapted to sense a physiological parameter of the subject, and the control unit is adapted to drive the electrode device to apply the stimulation responsive to the sensed physiological parameter.

There is further provided, in accordance with an embodiment of the present invention, apparatus for treating a subject, including:

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply electrical stimulation to the site, and configure the stimulation to reduce a probability of an occurrence of atrial fibrillation (AF).

For some applications, the control unit is configured to substantially continuously drive the electrode device to apply the stimulation during an application period lasting at least about 3 weeks. For some applications, in an operating mode of the control unit, the control unit is adapted to drive the electrode device to apply the stimulation during an application period lasting at least about 3 weeks, and to configure the stimulation such that, during the period, a longest duration of time in which no stimulation is applied is less than 4 hours.

For some applications, the apparatus includes a sensor, adapted to sense a physiological parameter of the subject, and the control unit is adapted to drive the electrode device to apply the stimulation responsive to the sensed physiological parameter.

There is still further provided, in accordance with an embodiment of the present invention, a method for treating a subject, including:

applying electrical stimulation to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the stimulation to prevent an occurrence of atrial fibrillation (AF).

There is additionally provided, in accordance with an embodiment of the present invention, a method for treating a subject, including:

applying an electrical stimulation to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the stimulation to reduce a probability of an occurrence of atrial fibrillation (AF).

There is yet additionally provided, in accordance with an embodiment of the present invention, treatment apparatus, including:

an electrode device, adapted to be coupled to a site of a subject suffering from atrial fibrillation (AF), the site selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

a pacing device, adapted to be applied to a heart of the subject; and a control unit, adapted to:

drive the electrode device to apply an electrical current to the site, drive the pacing device to apply a pacing signal to the heart, and configure the current and the pacing signal so as to treat the AF.

For some applications, the control unit is adapted to configure the pacing signal to have a pulse repletion interval having a duration of between about 50% and about 200% of an atrial refractory period of the subject For some applications, the control unit is adapted to configure the pacing signal to have a pulse repetition interval having a duration of between about 15 ms and about 190 ms.

For some applications, the control unit is adapted to configure the current to modulate an atrial refractory period of the subject.

For some applications, the control unit is adapted to modulate at least one parameter selected from the list consisting of: a parameter of the current, and a parameter of the pacing signal.

There is also provided, in accordance with an embodiment of the present invention, a treatment method, including:

applying an electrical current to a site of a subject suffering from atrial fibrillation (AF), the site selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

applying a pacing signal to a heart of the subject; and configuring the current and the pacing signal so as to treat the AF.

The present invention will be more fully understood from the following detailed description of embodiments thereof, taken together with the drawings, in which:

BRIEF DESCRIPTION OF THE DRAWINGS

FIG. 3A is a simplified cross-sectional illustration of a multipolar electrode device applied to a vagus nerve, in accordance with an embodiment of the present invention;

FIG. 3B is a simplified cross-sectional illustration of a generally-cylindrical electrode device applied to a vagus nerve, in accordance with an embodiment of the present invention;

FIG. 3C is a simplified perspective illustration of the electrode device of FIG. 3A, in accordance with an embodiment of the present invention;

FIG. 4 is a simplified perspective illustration of a multipolar point electrode device applied to a vagus nerve, in accordance with an embodiment of the present invention;

DETAILED DESCRIPTION OF EMBODIMENTS

Figure 1:
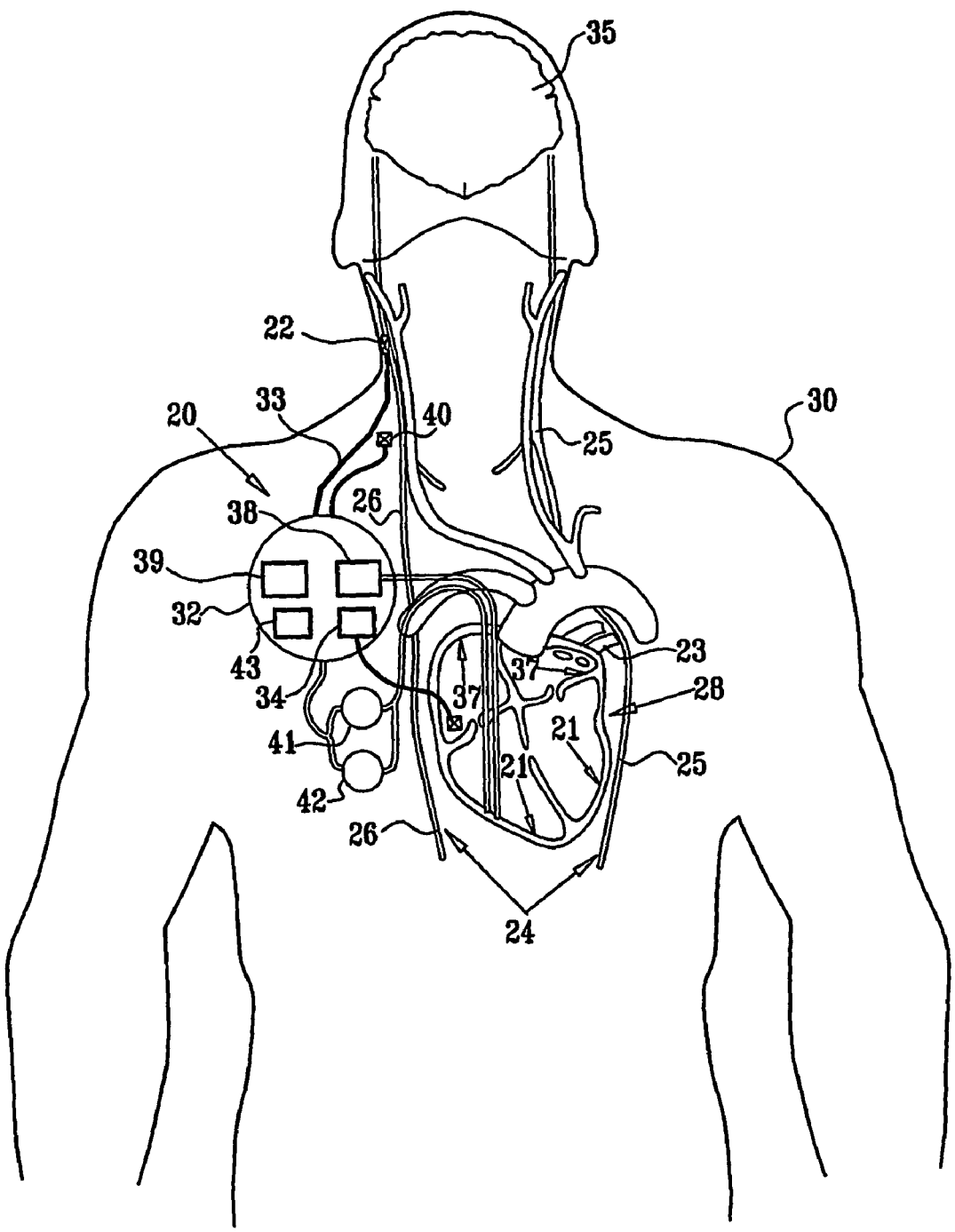
FIG. 1 is a schematic illustration of apparatus for treating a patient suffering from atrial fibrillation (AF), in accordance with an embodiment of the present invention.

FIG. 1 is a schematic illustration of apparatus 20 for treating a patient 30 suffering from atrial fibrillation (AF), in accordance with an embodiment of the present invention. Apparatus 20 comprises at least one electrode device 22, which is applied to a vagus nerve 24 (either a left vagus nerve 25 or a right vagus nerve 26), which innervates a heart 28 of patient 30. Apparatus 20 further comprises an implanted or external control unit 32, which typically communicates with electrode device 22 over a set of leads 33. For some applications, apparatus 20 comprises two electrode devices 22, one of which is applied to left vagus nerve 25, and the other to right vagus nerve 26. Alternatively or additionally, apparatus 20 comprises an electrical stimulator 34, which typically comprises one or more electrodes, and which is adapted to electrically stimulate tissue of patient 30, such as cardiac tissue, epicardial fat pads, atrial tissue 37, ventricular tissue 21, pulmonary venous tissue 23, the carotid artery, the internal jugular vein, the carotid sinus, or the vena cava vein.

For some applications, as described hereinbelow, control unit 32 is adapted to drive electrode device 22 to apply signals to vagus nerve 26. Unless otherwise noted, the control unit configures these signals to induce the propagation of efferent nerve impulses towards heart 28. The control unit typically configures the signals based on the particular application, by setting one or more parameters of the signals, such as:

- frequency of pulses within a pulse burst, e.g., for n pulses during a burst lasting t milliseconds, the burst has a frequency of 1000 n/t Hz;
- amplitude;
- pulse width;
- number of pulses delivered per heartbeat (pulses per trigger, or PPT);
- duty cycle;
- pulse polarity; and
- timing within the cardiac cycle.

Control unit 32 is typically adapted to receive and analyze one or more sensed physiological parameters or other parameters of patient 30, such as heart rate, electrocardiogram (ECG), blood pressure, indicators of decreased cardiac contractility, cardiac output, norepinephrine concentration, baroreflex sensitivity, or motion of the patient. In order to receive these sensed parameters, control unit 32 may comprise, for example, an ECG monitor 38, connected to a site on the patient's body such as heart 28, for example using one or more subcutaneous sensors or ventricular and/or atrial intracardiac sensors. The control unit may also comprise an accelerometer 39 for detecting motion of the patient. Alternatively, ECG monitor 38 and/or accelerometer 39 comprise separate implanted devices placed external to control unit 32, and, optionally, external to the patients body. Alternatively or additionally, control unit 32 receives signals from one or more physiological sensors 40, such as blood pressure sensors. For some applications, control unit 32 comprises or is coupled to an implantable cardioverter defibrillator (ICD) 41 and/or a pacemaker 42 (e.g., a bi-ventricular or standard pacemaker).

In an embodiment of the present invention, control unit 32 drives electrode device 22 to apply an electrical current to vagus nerve 24, and drives pacemaker 42 to apply pacing signals to heart 28. The control unit configures the current and the pacing signals to treat the AF of patient 30. For some applications, the control unit configures pacemaker 42 to apply the pacing signals with pulse repetition intervals having a duration of between about 50% and about 200% of an atral refractory period of patient 30 (e.g., between about 15 ms and about 190 ms), so as to treat the AF. For some applications, the control unit configures the vagal stimulation current to modulate the atrial refractory period. For some applications, the control unit modulates one or more parameters of the vagal stimulation current and/or of the pacing signal, such as on/off time, amplitude, number of pulses, pulse repetition interval (i.e., the interval between the leading edges of two consecutive pulses), or other parameters described herein.

For some applications, control unit 32 is adapted to distinguish between AF and NSR, generally by analyzing an ECG signal generated by ECG monitor 38. In order to detect rapid atrial activity indicative of AF, the analysis may include one or more of the following:

- P-wave analysis;
- analysis of ventricular response rate and/or ventricular response variability,
- sensed pressure, such as atrial pressure, sensed venous pressure, and/or sensed arterial pressure;
- the relationship(s) between one or more of the sensed pressures and sensed ventricular contractions (in the case of arterial pressure, such relationship is an indication of pulse deficit); and/or
- analysis of the duration of the isoelectrical segment of the ECG, optionally using the technique described in the above-cited article by Wijffels et al., entitled, "Atrial fibrillation begets atrial fibrillation." A duration greater than a first threshold value is typically indicative of NSR, while a duration less than a second threshold value, the second threshold value less than or equal to the first threshold value, is typically indicative of AF.

Control unit 32 itself may perform this analysis, or it may transmit data for analysis by an external processor (not shown).

Typically, apparatus 20 is programmable by a physician, such as by using an external console wirelessly in communication with control unit 32. The apparatus typically provides notification of various occurrences, such as the initiation of AF, cardioversion, or a mechanical failure. The apparatus may provide such notifications by various means, including generating a tone, vibrating, and/or wirelessly communicating with a local or remote receiver, such as one located at a medical facility.

In an embodiment of the present invention, control unit 32 drives electrode device 22 to apply signals to vagus nerve 26, and configures the signals to maintain pre-existing AF, i.e., to prevent the return to normal sinus rhythm (NSR). Typically, stimulation is applied in bursts (i.e., a series of pulses), and typical signal parameters include a pulse amplitude of between about 2 and about 5 milliamps, such as about 3 milliamps, a pulse duration of between about 1 and about 3 milliseconds, such as about 2 milliseconds, a PPT of between about 1 and about 8 pulses per trigger, such as about 6 pulses per trigger, and a pulse repetition interval of between about 5 and about 90 milliseconds, such as about 70 milliseconds. Alternatively, the pulse duration is between about 0.5 and about 3 milliseconds, and/or the PPT is between about 1 and about 100 pulses per trigger. For some applications, a constant ventricular response is maintained, such as by using techniques described in the above-cited U.S. patent application Ser. No. 10/205,475 (US Patent Application Publication 2003/0045909), which is assigned to the assignee of the present patent application and is incorporated herein by reference, or by using other techniques known in the art. For some applications, if NSR returns despite vagal stimulation, the intensity of vagal stimulation is increased for a short period, in order to induce a return to AF. For example, the period may have a duration of about one minute, and the more intense stimulation may have an amplitude of 6 milliamps and a PPT of 6 pulses per trigger. Alternatively or additionally, vagal stimulation is applied, and/or the intensity of vagal stimulation is increased, upon detection of a complex in the subject's cardiac rhythm other than NSR. Further alternatively or additionally, stimulation is not synchronized with features of the cardiac cycle. In this case, example signal parameter include an amplitude of about 3 milliamps, a pulse width of about 1 millisecond, and a frequency of about 5 Hz.

Alternatively or additionally, in order to achieve AF maintenance, control unit 32 drives stimulator 34 to electrically stimulate cardiac tissue of patient 30, such as the fat pads or atrial tissue 37. Typically, the atria are rapidly electrically paced during such stimulation. Typically, the stimulation is applied at a frequency of at least about 3 Hz with an amplitude greater than the diastolic threshold.

Electrical techniques for initiating and maintaining AF in animals for experimental purposes are known in the art (see, for example, the articles by Friedrichs G S, Morillo et al., and Wijffels et al., entitled, "Atrial fibrillation begets atrial fibrillation," cited hereinabove). For example, in the article entitled, "Atrial fibrillation begets atrial fibrillation," Wijffels et al. describe a technique for initiating and maintaining AF in goats. In this technique, a set of recording electrodes and a set of stimulating electrodes are applied to both atria. An atrial cardiogram is continuously analyzed in order to distinguish between sinus rhythm and AF. When sinus rhythm is detected, a one-second burst of biphasic stimuli (having an interval of 20 ms, i.e., a frequency of 50 Hz, and four times diastolic threshold) is delivered using one or more of the stimulating electrodes. In an embodiment, this technique, with appropriate modifications for therapeutic application to human patients, is used to maintain AF in human patients suffering from AF for therapeutic purposes, as described herein. Other optional modifications of this technique include, but are not limited to:

using other techniques for detection of AF and NSR, such as those described hereinabove;

using other parameters for the applied stimuli. Typically, the stimulation is applied at a frequency of at least about 3 Hz; and/or applying all or a portion of the stimulating electrodes to other cardiac tissue, such as the fat pads.

Other AF initiation/maintenance techniques known in the art (including those described in Friedrichs G S and Morillo et al.), optionally with the modifications described immediately hereinabove, may also be used to maintain AF to treat AF in human patients.

In an embodiment of the present invention, AF maintenance is achieved by performing vagal stimulation in conjunction with cardiac tissue stimulation. Techniques for such dual stimulation may be used that are described in the above-cited articles by Friedrichs G S and Hayashi H et al.

In another embodiment of the present invention, AF is maintained using surgical techniques, such as creating an electrical blockade in the atrium. Examples of such surgical techniques used in animal models are described in the above-referenced article by Friedrichs, and can be readily adapted by those skilled in the art for use with the therapeutic AF maintenance techniques described herein. Alternatively or additionally, AF is maintained using chemical/pharmacological agents known in the art, such as those described by Friedrichs in animal models, with appropriate modifications for treating AF in human patients.

In an embodiment of the present invention, AF is maintained using techniques described in the above-cited articles by Preston and Moreira.

In an embodiment of the present invention, AF is maintained long-term, e.g., longer than about three weeks. Such AF maintenance generally reduces the frequency of recurring transitions between AF and NSR, which transitions are common in patients with AF, particularly in patients with chronic episodic AF. Such repeated transitions are generally undesirable because: (a) they often cause discomfort for the patient, (b) they may increase the risk of thromboembolic events, and (c) they often make prescribing an appropriate drug regimen difficult. Drug regimens that are beneficial for the patient when in AF are often inappropriate when the patient is in NSR, and vice versa. For example, beta blockers may help provide rate control for a patient when in AF, but may be harmful for the same patient when suffering bradycardia when in NSR. Knowledge that the patient will generally remain in AF typically helps a physician prescribe a more appropriate and/or lower-dosage drug regimen, in association with this embodiment. In addition, such AF maintenance may be beneficial for stabilizing a patient, such as a patient for whom cardioversion is not successful. For example, for many patients, electrical cardioversion alone is unsuccessful in maintaining NSR long-term (Fuster et al., cited hereinabove, write that after undergoing cardioversion, " . . . only 23% of the patients remained in sinus rhythm after 1 year and 16% after 2 years. . . . ").

In another embodiment of the present invention, AF is maintained short-term, typically between about one day and about three weeks. Such maintenance is generally beneficial during a period in which conventional anticoagulation drug therapy is applied to the patient prior to attempting electrical or pharmacological cardioversion. (Such a period may be desirable when an initial diagnosis of AF occurs more than 48 hours after initiation of AF, or an unknown amount of time after initiation of AF.) Cardioversion is generally not attempted during this period because of the particularly elevated risk of thromboembolic events before the anticoagulation therapy is effective. AF maintenance during this period to prevent naturally-occurring cardioversion, i.e., spontaneous reversion to NSR, is believed by the inventors to reduce the risk of thromboembolic events, such as stroke. Prior to attempting electrical or pharmacological cardioversion, the physician directs apparatus 20 to terminate AF maintenance.

In an embodiment of the present invention, control unit 32 drives electrode device 22 to apply signals to vagus nerve 24, and configures the signals so as to increase atrial motion. Such increased atrial motion typically causes mixing, such as by swirling or agitation of the blood in the atrium, which in turn is believed by the inventors to reduce the likelihood of coagulation and resultant thromboembolic events, including stroke (including in subjects having NSR). In an embodiment, control unit 32 modulates the vagal stimulation as follows:

during a "high" stimulation period, typically having a duration of between about 100 ms and about 1000 ms, the control unit configures the vagal stimulation so as to cause a reduction in the force of contraction of atrial cells; and during a "low" stimulation period, typically having a duration of between about 200 ms and about 15 seconds, the control unit configures the vagal stimulation so as to cause the atrial cells to contract with "rebound" strength (although, because of the AF, the atrial cells typically remain unsynchronized during this rebound contraction).

The resulting fluctuation in atrial contractility and pressure serves to mix the blood in the atria For example, (a) the "high" period may have the following parameters: a duration of about 100 ms, a stimulation amplitude of about 5 milliamps, a pulse duration of about 1 ms, and a frequency of about 30 Hz; and (b) the "low" period may have the following parameters: a duration of about 12 seconds, and a stimulation amplitude of 0 milliamps (i.e., no stimulation during the "low" period). In this example, about 3 pulses are applied during a 100-ms period that occurs every 12 seconds.

In an embodiment, the control unit synchronizes the "high" and "low" periods with one or more sensed physiological variables, such as characteristics of the cardiac cycle or respiratory cycle. For example, the control unit may (a) initiate the "high" stimulation period within about 50 milliseconds after the occurrence of a QRS-complex, or within about 500 milliseconds after the beginning of an expiration, or (b) synchronize the "low" stimulation period with diastole, i.e., when the ventricle is open, in order to maximize blood flow from the atria.

Typically, the control unit configures the stimulation to cycle continuously between "high" and "low" stimulation when applying the treatment. The parameters of the modulation may include one or more of the following:

frequency—the stimulation is applied at a higher frequency during the "high" stimulation period than during the "low" stimulation period. For example, the "high" frequency may be about 20 Hz, while the "low" frequency may be about 1 Hz;

amplitude—the stimulation is applied with a higher amplitude during the "high" stimulation period than during the "low" stimulation period. For example, the "high" amplitude may be about 6 milliamps, while the "low" amplitude may be about 2 milliamps;

on/off—the stimulation is applied only during the "high" stimulation period;

induce/block—the stimulation is configured to induce action potentials in the vagus nerve during the "high" stimulation period, and to block action potentials in the vagus nerve during the "low" stimulation period;

pulse width—the stimulation is applied with a greater pulse width during the "high" stimulation period than during the "low" stimulation period. For example, the "high" pulse width may be about 1 ms, while the "low" pulse width may be about 0.2 ms; and/or pulses per trigger (PPT)—the stimulation is applied at a higher PPT during the "high" stimulation period than during the "low" stimulation period. For example, the "high" PPT may be about 3 pulses per trigger, while the "low" PPT may be about 1 pulse per trigger.

Alternatively or additionally, control unit 32 increases atrial motion by electrical stimulation of cardiac tissue, such as atrial tissue or fat pads. Stimulation of left atrial tissue is typically achieved either by directly placing an electrode at or above the left auricle, or by stimulating the interatrial septum, the vena cava (e.g., in the area of the Ligament of Marshall), or the coronary sinus. Controllable parameters of such stimulation typically include frequency, amplitude, and/or on/off. For some applications, vagal and/or cardiac tissue stimulation is configured to improve blood flow out of the left atrial auricle. For example, electrical stimulation may be applied to the left atrial auricle for a short period during diastole at a frequency of at least about 3 Hz and at an amplitude greater than diastolic threshold.

For some applications, atrial motion is increased using the techniques described herein upon the termination of AF, for example, to prevent or treat electro-mechanical-dissociation (EMD), in which cardiac electrical activity is not coupled with appropriate mechanical contraction. Alternatively, atrial motion is increased using the techniques described herein in a patient who has not suffered from AF.

In an embodiment of the present invention, control unit 32 drives electrode device 22 to apply signals to vagus nerve 24, and configures the signals so as to restore NSR, i.e., to induce cardioversion. According to a first approach for restoring NSR, the configuration includes repeatedly changing parameters of the stimulation. The parameters changed may include one or more of the following:

intensity of stimulation (amplitude and/or frequency)—the strength of the stimulation is switched between stronger and weaker intensities;

on/off—the stimulation is configured to switch between applying stimulation and not applying stimulation, and/or a duration of an "on" period and/or an "off" period of the stimulation is varied;

pulse width of the stimulation; and/or induce/block—the stimulation is configured to switch between inducing action potentials in the vagus nerve and blocking action potentials in the vagus nerve.

Typically, control unit 32 cycles between application of the different parameters at a rate of between about the duration of one heart beat and about 30 seconds. For some applications, the control unit performs the switching according to a predetermined pattern. For other applications, the control unit performs the switching randomly, with a typical interval between changes of between about 500 milliseconds and about 30 seconds.

Such switching of the stimulation is believed by the inventors to cause fluctuations in the atrial effective refractory period (AERP), thereby breaking reentry cycles and restoring synchronization and NSR. The inventors hypothesize that although the effect of vagal stimulation on the atria is generally heterogeneous in nature (not all areas of the atria receive the same stimulus), rapid switching of the stimulation, i.e., the application of heterogeneous stimuli, causes an overall atrial response that is more homogenous. The inventors further hypothesize that such atrial cell synchronization is due in part to: (a) more frequent activation of atrial cells because of the reduced refractory period caused by the vagal stimulation, and/or (b) the breaking of re-entry circuits during the brief periods when weak, blocking, or no vagal stimulation is applied.

According to a second approach for restoring NSR, control unit 32:

during a first period, typically having a duration between about 500 milliseconds and about 30 seconds, (a) paces the heart using conventional pacing techniques, such as by driving conventional pacemaker 42 to apply pacing signals to the heart, e.g., to the right atrium, right ventricle, or both ventricles, and, simultaneously, (b) configures the signals applied to the vagus nerve to provide generally constant vagal stimulation, i.e., without varying parameters of the stimulation, with a high intensity.

Pacing of the heart is generally necessary because such high-intensity vagal stimulation would otherwise severely slow the heart rate; and during a second period, suddenly ceases vagal stimulation. Such sudden cessation generally destabilizes the atrial cells, resulting in a return to NSR. The destabilization may be thought of as analogous to that achieved by conventional electrical cardioversion. The pacing is also generally terminated during the second period, typically simultaneously with, or up to about 30 seconds after, cessation of vagal stimulation. Alternatively, the pacing is terminated upon restoration of atrial activity.

The control unit may be configured to repeat this stimulation/pacing—sudden cessation cycle, if necessary to restore NSR.

A third approach is typically appropriate for treating AF principally caused by heightened adrenergic tone. When atrial fibrillation is induced by adrenergic tone, vagal stimulation generally reduces the net adrenergic effect by slowing the heart rate and by antagonizing the adrenergic system. According to this third approach, control unit 32 drives electrode device 22 to apply signals to vagus nerve 24, and configures the signals to apply substantially constant vagal stimulation, i.e., without varying parameters of the stimulation, so as to restore NSR In this approach, the control unit typically does not use feedback in order to vary the parameters of stimulation. Parameters typically appropriate for such stimulation include: (a) application of a single pulse or a single burst of pulses each heart beat, (b) a pulse width of between about 0.5 ms and about 1.5 ms, and (c) a PPT of between about 1 and about 10. The amplitude of the applied signal is typically dependant upon the specific electrode device used for the treatment.

For all three of these approaches, the control unit may be configured to apply the cardioversion treatment: (a) upon detection of AF, (b) upon receiving an operator command, such as from a health care worker, or (c) at some other time. For some applications, the control unit applies the treatment at a certain time of day and/or when a patient motion signal received from accelerometer 39 indicates that the patient is at rest.

In an embodiment of the present invention, apparatus 20 is adapted to be used during conventional electrical atrial defibrillation. Control unit 32 drives electrode device 22 to apply stimulating signals to vagus nerve 24, and configures the stimulating signals to cause severe bradycardia and a decreased level of alertness during the defibrillation. Such severe bradycardia generally causes the patient to partially lose consciousness and thereby experience less pain during the defibrillation. Apparatus 20 thus can be thought of as a vagus nerve facilitated tranquilizer. Parameters for such stimulation are typically similar to those appropriate for heart rate reduction, however, with increased PPT. For example, such parameters may include a pulse width of between about 1 and about 3 milliseconds, such as about 2 milliseconds, an amplitude of between about 4 and about 8 milliamps, such as about 6 milliamps, and a PPT of between about 6 and about 10 pulses per trigger, such as about 8 pulses per trigger. Alternatively or additionally, parameters disclosed in the above-referenced U.S. patent application Ser. No. 10/205,475 are used. For some applications, apparatus 20 comprises conventional pacemaker 42, which is used to pace the heart in the event of excessive bradycardia caused by the vagal stimulation.

For some tranquilizing applications, control unit 32 additionally applies inhibiting signals to the vagus nerve, and configures the inhibiting signals to block vagal pain afferents, thereby further reducing pain experienced by the patient during the defibrillation. Techniques for selectively blocking pain sensations may be used that are described in (a) U.S. patent application Ser. No. 09/824,682, filed Apr. 4, 2001, entitled, "Method and apparatus for selective control of nerve fibers," (b) PCT Patent Application PCT/IL02/00068, filed Jan. 23, 2002, entitled, "Treatment of disorders by unidirectional nerve stimulation," and/or (c) U.S. patent application Ser. No. 09/944,913, filed Aug. 31, 2001, entitled, "Treatment of disorders by unidirectional nerve stimulation," all of which are assigned to the assignee of the present patent application and are incorporated herein by reference.

Figure 2:
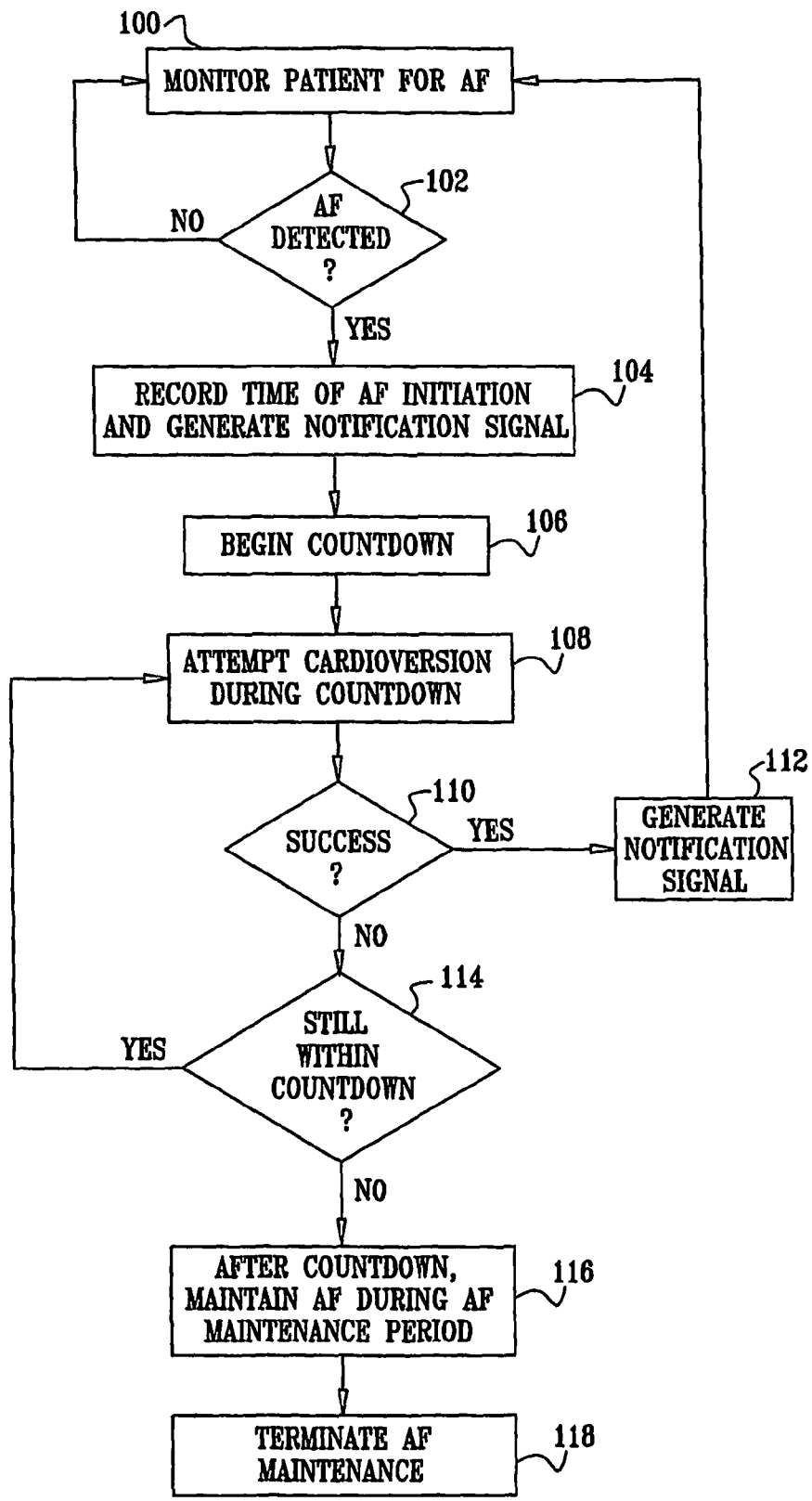
FIG. 2 is a flow chart that schematically illustrates a method for determining and applying an appropriate AF treatment based on a countdown, in accordance with an embodiment of the present invention.

FIG. 2 is a flow chart that schematically illustrates a method for determining and applying an appropriate AF treatment based on a countdown, in accordance with an embodiment of the present invention. In this embodiment, apparatus 20 additionally comprises a timer 43, which optionally is integrated in software of control unit 32 (FIG. 1). Alternatively, the functions of timer 43 may be implemented in circuitry of control unit 32. At an AF monitoring step 100, apparatus 20 monitors patient 30 for indications of AF, such as by using one or more of the AF detection techniques described hereinabove. So long as AF is not detected at an AF check step 102, the method returns to step 100. On the other hand, if AF is detected, control unit 32 records the time of initiation of the AF and optionally generates a notification signal, at a recording and notification step 104.

The control unit is typically adapted to report the recorded time of AF initiation and/or countdown time upon interrogation by a physician. If the patient seeks medical care after generation of the notification signal in step 104, the physician typically considers the recorded AF initiation time when determining the appropriate therapy. If the physician opts to attempt conventional cardioversion, the physician may reset the apparatus to resume monitoring for AF at step 100. Alternatively, the physician may opt to allow the device to continue its therapeutic course at step 106, as follows.

The control unit activates timer 43 to begin a countdown, at a countdown step 106. The countdown typically has a duration from the detection of AF of between about 24 and 54 hours, such as 48 hours. During the countdown, apparatus 20 typically attempts to restore NSR, using the cardioversion techniques and apparatus described herein, or other methods and apparatus known in the art, such as ICD 41. After attempting to restore NSR, at a success check step 110, the apparatus determines whether NSR has been successfully restored and maintained, such as by using one or more of the AF detection techniques described hereinabove. If NSR has been restored, the apparatus typically generates a notification signal to the patient and/or healthcare worker, at a notification generation step 112. The apparatus then resumes monitoring the patient for subsequent AF, at step 100.

On the other hand, if NSR has not been restored, then the apparatus checks whether the countdown has been completed, at a countdown check step 116. If the countdown has not been completed, the apparatus again attempts cardioversion, at step 108. For some applications, the apparatus is configured to pause between cardioversion attempts, and/or to make only a certain number of cardioversion attempts, typically based on programmed parameters and/or physiological parameters measured in real time. If, on the other hand, the countdown has concluded, the apparatus attempts to maintain AF, typically using AF maintenance techniques described herein, at an AF maintenance step 116. By minimizing or preventing undesired spontaneous transitions into NSR, the apparatus may reduce the risk of thromboembolic events, such as stroke. AF maintenance typically continues until a physician intervenes by signaling the apparatus to terminate maintenance, at an AF maintenance termination step 118.

For some applications, apparatus 20 is used with this countdown method in order to implement a set of clinical guidelines for treatment of AF. For example, the above-cited ACC/AHA/ESC practice guidelines for AF suggest that immediate cardioversion be attempted when AF has been present for less than 48 hours, but that the patient receive anticoagulation therapy for three to four weeks before cardioversion is attempted if the AF has been present for more than 48 hours. Such an anticoagulation period is also recommended when the duration of AF is unknown, for example, because the patient may have been asymptomatic for a period of time after initiation of AF. The use of this countdown method generally eliminates this unknown, thereby sometimes allowing beneficial cardioversion to be performed immediately rather than after three to four weeks of an anticoagulation drug regimen.

In an embodiment of the present invention, means are employed for avoiding bradycardia, which may be induced in response to application of some of the techniques described herein. Such means include, but are not limited to:

Applying stimulation only when the heart rate of the subject is greater than a minimum threshold, e.g., 60 beats per minute;

In the event that the heart rate drops below a threshold rate, e.g., 60 beats per minute, the heart is paced using conventional pacing techniques, such as by driving conventional pacemaker 42 to apply pacing signals to the heart, e.g., to the right atrium, right ventricle, or both ventricles, in order to keep the heart rate at or above the threshold value; and Monitoring heart rate after applying stimulation. Upon detection that heart rate has fallen below a threshold rate, e.g., 60 beats per minute, during the following application of stimulation one or more parameters of the stimulation are adjusted so as to reduce the strength of the stimulation. For some applications, this technique is applied periodically or continuously while applying stimulation.

For many of the applications of vagal stimulation described herein, electrode device 22 typically comprises one or more electrodes, such as monopolar, bipolar or tripolar electrodes. Electrode device 22 is typically placed: (a) around vagus nerve 24, (b) around vagus nerve 24 and the carotid artery (configuration not shown), or (c) inside the carotid artery in a position suitable for vagal stimulation (not shown). Depending on the particular application, one or more electrode devices 22 may be positioned to stimulate the left or right vagus nerve, either above or below the cardiac branch bifurcation. For some applications, the electrodes comprise cuff electrodes, ring electrodes, and/or point electrodes. Typically, the electrodes stimulate the nerve without coming in direct contact therewith, by applying an electrical field to the nerve. Alternatively, the electrodes stimulate the nerve by coming in direct contact therewith. For applications in which excitatory signals are applied to vagus nerve 24 (as opposed to inhibiting signals), control unit 32 typically configures the signals to induce the propagation of efferent nerve impulses towards heart 28.

In some embodiments of the present invention, when configuring vagal stimulation to induce the propagation of efferent nerve impulses towards heart 28, control unit 32 drives electrode device 22 to (a) apply signals to induce the propagation of efferent nerve impulses towards heart 28, and (b) suppress artificially-induced afferent nerve impulses towards a brain 35 of the patient (FIG. 1), in order to minimize unintended side effects of the signal application.

FIG. 3A is a simplified cross-sectional illustration of a generally-cylindrical electrode device 22 applied to vagus nerve 24, in accordance with an embodiment of the present invention. Electrode device 22 comprises a central cathode 46 for applying a negative current ("cathodic current") in order to stimulate vagus nerve 24, as described below. Electrode device 22 additionally comprises a set of one or more anodes 44 (44a, 44b, herein: "efferent anode set 44"), placed between cathode 46 and the edge of electrode device 22 closer to heart 28 (the "efferent edge").

Efferent anode set 44 applies a positive current ("efferent anodal current") to vagus nerve 24, for blocking action potential conduction in vagus nerve 24 induced by the cathodic current, as described below. Typically, electrode device 22 comprises an additional set of one or more anodes 45 (45a, 45b, herein: "afferent anode set 45"), placed between cathode 46 and the edge of electrode device 22 closer to brain 35. Afferent anode set 45 applies a positive current ("afferent anodal current") to vagus nerve 24, in order to block propagation of action potentials in the direction of the brain during application of the cathodic current.

For some applications, the one or more anodes of efferent anode set 44 are directly electrically coupled to the one or more anodes of afferent anode set 45, such as by a common wire or shorted wires providing current to both anode sets, substantially without any intermediary elements. Typically, the sizes of the anodes and/or distances of the various anodes from the nerve are regulated so as to produce desired ratios of currents delivered through the various anodes. In these applications, central cathode 46 is typically placed closer to one of the anode sets than to the other, for example, so as to induce asymmetric stimulation (i.e., not necessarily unidirectional in all fibers) between the two sides of the electrode device. The closer anode set typically induces a stronger blockade of the cathodic stimulation.

Reference is now made to FIG. 3B, which is a simplified cross-sectional illustration of a generally-cylindrical electrode device 240 applied to vagus nerve 24, in accordance with an embodiment of the present invention. Electrode device 240 comprises exactly one efferent anode 244 and exactly one afferent anode 245, which are electrically coupled to each other, such as by a common wire 250 or shorted wires providing current to both anodes 244 and 245, substantially without any intermediary elements. (For some applications, electrode device 240 comprises more than one efferent anode 244 and/or more than one afferent anode 245.) The cathodic current is applied by a cathode 246 with an amplitude sufficient to induce action potentials in large- and medium-diameter fibers (e.g., A- and B-fibers), but insufficient to induce action potentials in small-diameter fibers (e.g., C-fibers).

Reference is again made to FIG. 3A. Cathode 46 and anode sets 44 and 45 (collectively, "electrodes") are typically mounted in a housing such as an electrically-insulating cuff 48 and separated from one another by insulating elements such as protrusions 49 of the cuff. Typically, the width of the electrodes is between about 0.5 and about 2 millimeters, or is equal to approximately one-half the radius of the vagus nerve. The electrodes are typically recessed so as not to come in direct contact with vagus nerve 24. For some applications, such recessing enables the electrodes to achieve generally uniform field distributions of the generated currents and/or generally uniform values of the activation function defined by the electric potential field in the vicinity of vagus nerve 24. Alternatively or additionally, protrusions 49 allow vagus nerve 24 to swell into the canals defined by the protrusions, while still holding the vagus nerve centered within cuff 48 and maintaining a rigid electrode geometry. For some applications, cuff 48 comprises additional recesses separated by protrusions, which recesses do not contain active electrodes. Such additional recesses accommodate swelling of vagus nerve 24 without increasing the contact area between the vagus nerve and the electrodes. For some applications, the distance between the electrodes and the axis of the vagus nerve is between about 1 and about 4 millimeters, and is greater than the closest distance from the ends of the protrusions to the axis of the vagus nerve. Typically, protrusions 49 are relatively short (as shown). The distance between the ends of protrusions 49 and the center of the vagus nerve is typically between about 1 and 3 millimeters. (Generally, the diameter of the vagus nerve is between about 2 and 3 millimeters.) Alternatively, for some applications, protrusions 49 are longer and/or the electrodes are placed closer to the vagus nerve in order to reduce the energy consumption of electrode device 22.

In an embodiment of the present invention, efferent anode set 44 comprises a plurality of anodes 44, typically two anodes 44a and 44b, spaced approximately 0.5 to 2.0 millimeters apart. Application of the efferent anodal current in appropriate ratios from the plurality of anodes generally minimizes the "virtual cathode effect," whereby application of too large an anodal current stimulates rather than blocks fibers. In an embodiment, anode 44a applies a current with an amplitude equal to about 0.5 to about 5 milliamps (typically one-third of the amplitude of the current applied by anode 44b).

Anode 44a is typically positioned in cuff 48 to apply current at the location on vagus nerve 24 where the virtual cathode effect is maximally generated by anode 44b. For applications in which the blocking current through anode 44b is expected to vary substantially, efferent anode set 44 typically comprises a plurality of virtual-cathode-inhibiting anodes 44a, one or more of which is activated at any time based on the expected magnitude and location of the virtual cathode effect.

Likewise, afferent anode set 45 typically comprises a plurality of anodes 45, typically two anodes 45a and 45b, in order to minimize the virtual cathode effect in the direction of the brain. In certain electrode configurations, cathode 46 comprises a plurality of cathodes in order to minimize the "virtual anode effect," which is analogous to the virtual cathode effect.

FIG. 3C is a simplified perspective illustration of electrode device 22, in accordance with an embodiment of the present invention. When applied to vagus nerve 24, electrode device 22 typically encompasses the nerve. As described, control unit 32 typically drives electrode device 22 to (a) apply signals to vagus nerve 24 in order to induce the propagation of efferent action potentials towards heart 28, and (b) suppress artificially-induced afferent action potentials towards brain 35. The electrodes typically comprise ring electrodes adapted to apply a generally uniform current around the circumference of the nerve, as best shown in FIG. 3C.

FIG. 4 is a simplified perspective illustration of a multipolar point electrode device 140 applied to vagus nerve 24, in accordance with an embodiment of the present invention. In this embodiment, anodes 144a and 144b and a cathode 146 typically comprise point electrodes (typically 2 to 100), fixed inside an insulating cuff 148 and arranged around vagus nerve 24 so as to selectively stimulate nerve fibers according to their positions inside the nerve. In this case, techniques described in the above-cited articles by Grill et al., Goodall et al., and/or Veraart et al. may be used. The point electrodes typically have a surface area between about 0.01 mm2 and 1 mm2. In some applications, the point electrodes are in contact with vagus nerve 24, as shown, while in other applications the point electrodes are recessed in cuff 148, so as not to come in direct contact with vagus nerve 24, similar to the recessed ring electrode arrangement described above with reference to FIG. 3A. For some applications, one or more of the electrodes, such as cathode 146 or anode 144a, comprise a ring electrode, as described with reference to FIG. 3C, such that electrode device 140 comprises both ring electrode(s) and point electrodes (configuration not shown). Additionally, electrode device 22 optionally comprises an afferent anode set (positioned like anodes 45a and 45b in FIG. 3A), the anodes of which comprise point electrodes and/or ring electrodes.

Alternatively, ordinary, non-cuff electrodes are used, such as when the electrodes are placed on the epicardial fat pads instead of on the vagus nerve.

Figure 5:
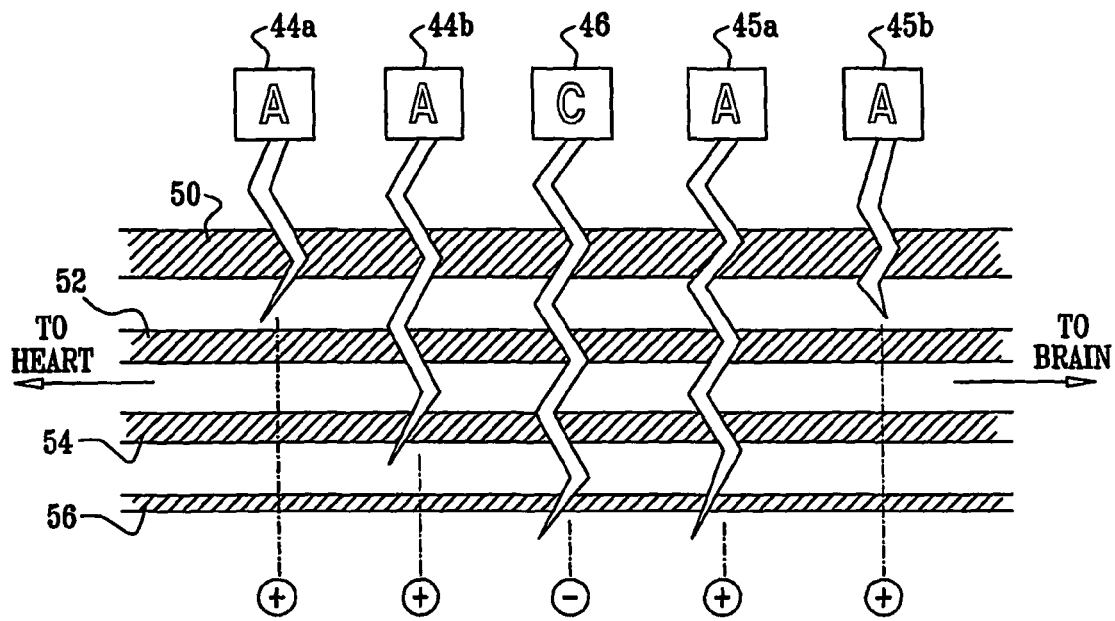
FIG. 5 is a conceptual illustration of the application of current to a vagus nerve, in accordance with an embodiment of the present invention.

FIG. 5 is a conceptual illustration of the application of current to vagus nerve 24 in order to achieve smaller-to-larger diameter fiber recruitment, in accordance with an embodiment of the present invention. When inducing efferent action potentials towards heart 28, control unit 32 drives electrode device 22 to selectively recruit nerve fibers beginning with smaller-diameter fibers and to progressively recruit larger-diameter fibers as the desired stimulation level increases. This smaller-to-larger diameter recruitment order mimics the body's natural order of recruitment.

Typically, in order to achieve this recruitment order, the control unit stimulates myelinated fibers essentially of all diameters using cathodic current from cathode 46, while simultaneously inhibiting fibers in a larger-to-smaller diameter order using efferent anodal current from efferent anode set 44. For example, FIG. 5 illustrates the recruitment of a single, smallest nerve fiber 56, without the recruitment of any larger fibers 50, 52 and 54. The depolarizations generated by cathode 46 stimulate all of the nerve fibers shown, producing action potentials in both directions along all the nerve fibers. Efferent anode set 44 generates a hyperpolarization effect sufficiently strong to block only the three largest nerve fibers 50, 52 and 54, but not fiber 56. This blocking order of larger-to-smaller diameter fibers is achieved because larger nerve fibers are inhibited by weaker anodal currents than are smaller nerve fibers. Stronger anodal currents inhibit progressively smaller nerve fibers. When the action potentials induced by cathode 46 in larger fibers 50, 52 and 54 reach the hyperpolarized region in the larger fibers adjacent to efferent anode set 44, these action potentials are blocked. On the other hand, the action potentials induced by cathode 46 in smallest fiber 56 are not blocked, and continue traveling unimpeded toward heart 28. Anode pole 44a is shown generating less current than anode pole 44b in order to minimize the virtual cathode effect in the direction of the heart, as described above.

When desired, in order to increase the parasympathetic stimulation delivered to the heart, the number of fibers not blocked is progressively increased by decreasing the amplitude of the current applied by efferent anode set 44. The action potentials induced by cathode 46 in the fibers now not blocked travel unimpeded towards the heart. As a result, the parasympathetic stimulation delivered to the heart is progressively increased in a smaller-to-larger diameter fiber order, mimicking the body's natural method of increasing stimulation. Alternatively or additionally, in order to increase the number of fibers stimulated, while simultaneously decreasing the average diameter of fibers stimulated, the amplitudes of the currents applied by cathode 46 and efferent anode set 44 are both increased (thereby increasing both the number of fibers stimulated and blocked). In addition, for any given number of fibers stimulated (and not blocked), the amount of stimulation delivered to the heart can be increased by increasing the PPT, frequency, and/or pulse width of the current applied to vagus nerve 24.

In order to suppress artificially-induced afferent action potentials from traveling towards the brain in response to the cathodic stimulation, control unit 32 typically drives electrode device 22 to inhibit fibers 50, 52, 54 and 56 using afferent anodal current from afferent anode set 45. When the afferent-directed action potentials induced by cathode 46 in all of the fibers reach the hyperpolarized region in all of the fibers adjacent to afferent anode set 45, the action potentials are blocked. Blocking these afferent action potentials generally minimizes any unintended side effects, such as undesired or counterproductive feedback to the brain, that might be caused by these action potentials. Anode 45b is shown generating less current than anode 45a in order to minimize the virtual cathode effect in the direction of the brain, as described above.

In an embodiment of the present invention, the amplitude of the cathodic current applied in the vicinity of the vagus nerve is between about 2 milliamps and about 10 milliamps. Such a current is typically used in embodiments that employ techniques for achieving generally uniform stimulation of the vagus nerve, i.e., stimulation in which the stimulation applied to fibers on or near the surface of the vagus nerve is generally no more than about four times greater than stimulation applied to fibers situated more deeply in the nerve. This corresponds to stimulation in which the value of the activation function at fibers on or near the surface of the vagus nerve is generally no more than about four times greater than the value of the activation function at fibers situated more deeply in the nerve. For example, as described hereinabove with reference to FIG. 3A, the electrodes may be recessed so as not to come in direct contact with vagus nerve 24, in order to achieve generally uniform values of the activation function. Typically, but not necessarily, embodiments using approximately 5 mA of cathodic current have the various electrodes disposed between about 0.5 mm and about 2.5 mm from the axis of the vagus nerve. Alternatively, larger cathodic currents (e.g., 10-30 mA) are used in combination with electrode distances from the axis of the vagus nerve of greater than 2.5 mm (e.g., 2.5-4.0 mm), so as to achieve an even greater level of uniformity of stimulation of fibers in the vagus nerve.

In an embodiment of the present invention, the cathodic current is applied by cathode 46 with an amplitude sufficient to induce action potentials in large- and medium-diameter fibers 50, 52, and 54 (e.g., A- and B-fibers), but insufficient to induce action potentials in small-diameter fibers 56 (e.g., C-fibers). Simultaneously, an anodal current is applied by anode 44b in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked by anode 45a, as described above. Alternatively, the afferent anodal current is configured to not fully block afferent action potentials, or is simply not applied. In these cases, artificial afferent action potentials are nevertheless generally not generated in C-fibers, because the applied cathodic current is not strong enough to generate action potentials in these fibers.

These techniques for efferent stimulation of only B-fibers are typically used in combination with techniques described hereinabove for achieving generally uniform stimulation of the vagus nerve. Such generally uniform stimulation enables the use of a cathodic current sufficiently weak to avoid stimulation of C-fibers near the surface of the nerve, while still sufficiently strong to stimulate B-fibers, including B-fibers situated more deeply in the nerve, i.e., near the center of the nerve. For some applications, when employing such techniques for achieving generally uniform stimulation of the vagus nerve, the amplitude of the cathodic current applied by cathode 46 may be between about 3 and about 10 milliamps, and the amplitude of the anodal current applied by anode 44b may be between about 1 and about 7 milliamps. (Current applied at a different site and/or a different time is used to achieve a net current injection of zero.)

For some applications, control unit 32 is adapted to receive feedback from one or more of the electrodes in electrode device 22, and to regulate the signals applied to the electrode device responsive thereto. For example, control unit 32 may analyze amplitudes of various peaks in a compound action potential (CAP) signal recorded by the electrodes, in order to determine a relative proportion of stimulated larger fibers (having faster conduction velocities) to smaller fibers (having slower conduction velocities). Alternatively or additionally, control unit 32 analyzes an area of the CAP, in order to determine an overall effect of the stimulation. In an embodiment, the feedback is received by electrodes other than those used to apply signals to the nerve.

Figure 6:
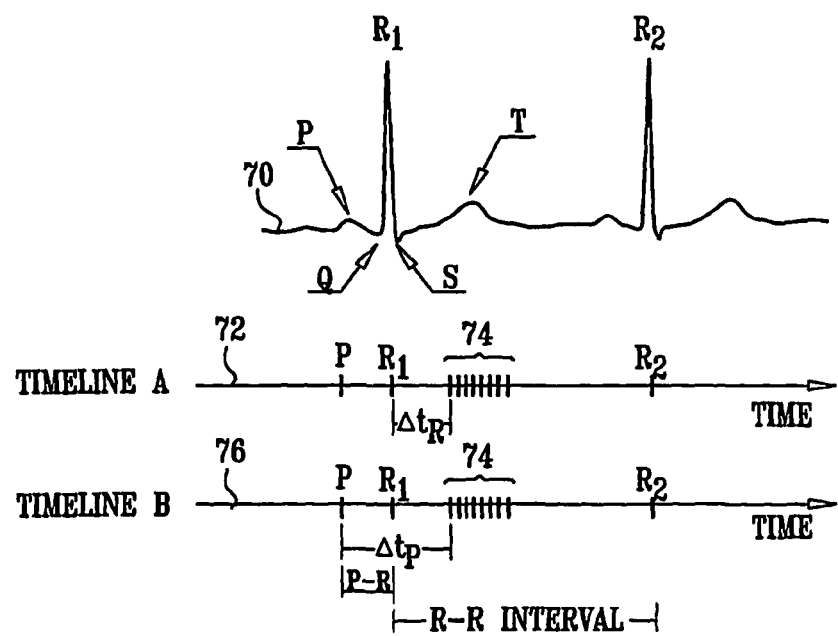
FIG. 6 is a simplified illustration of an electrocardiogram (ECG) recording and of example timelines showing the timing of the application of a burst of stimulation pulses, in accordance with an embodiment of the present invention.

FIG. 6 is a simplified illustration of an ECG recording 70 and example timelines 72 and 76 showing the timing of the application of a burst of stimulation pulses 74, in accordance with an embodiment of the present invention. The application of the burst of pulses in each cardiac cycle typically commences after a variable delay after a trigger such as a detected R-wave, P-Wave, or other feature of an ECG. For some applications, other parameters of the applied burst of pulses are also varied in real time. Such other parameters include amplitude, number of pulses per trigger (PPT), pulse duration, and pulse repetition interval. For some applications, the delay and/or one or more of the other parameters are calculated in real time using a function, the inputs of which include one or more pre-programmed but updateable constants and one or more sensed parameters, such as the R-R interval between cardiac cycles and/or the P-R interval.

The variable delay before applying pulse burst 74 in each cardiac cycle can be determined from a number of sensed physiological parameters ("initiation physiological parameters"), including sensed points in the cardiac cycle, including P-, Q-, R-, S- and T-waves. Typically the delay is measured from the P-wave, which indicates atrial contraction. Alternatively, the delay is measured from the R-wave, particularly when the P-wave is not easily detected. Timeline A 72 and Timeline B 76 show the delays, $\Delta t_R$ and $\Delta t_P$ measured from R and P, respectively.

In an embodiment, a look-up table of parameters, such as delays (e.g., $\Delta t$) and/or other parameters, is used to determine in real time the appropriate parameters for each application of pulses, based on the one or more sensed parameters, and/or based on a predetermined sequence stored in the lookup table. For example, in embodiments of the present invention in which the control unit configures signals applied to the vagus nerve so as to induce cardioversion, such a predetermined sequence may include delays of alternating longer and shorter durations.

Optionally, the stimulation applied by vagal stimulation apparatus 20 is applied in conjunction with or separately from stimulation of sympathetic nerves innervating the heart. For example, vagal inhibition described herein and/or periods of non-stimulation of the vagus nerve described herein may be replaced or supplemented by excitation of sympathetic nerves. Such sympathetic stimulation can be applied using techniques of smaller-to-larger diameter fiber recruitment, as described herein, or other nerve stimulation techniques known in the art.

Alternatively or additionally, the techniques of smaller-to-larger diameter fiber recruitment and Δt control are applied in conjunction with methods and apparatus described in one or more of the patents, patent applications, articles and books cited herein.

Although some embodiments of the present invention are described herein with respect to applying a designated electrical current to tissue of a patient, this is to be understood in the specification and in the claims as including creating a designated voltage drop between two or more electrodes.

Although embodiments of the present invention described hereinabove with reference to FIGS. 3A, 3B, 3C, 4 and 5 are described with reference to the vagus nerve, the electrode devices of these embodiments may also be applied to other nerves for some applications.

In some embodiments, techniques described herein are applied in combination with techniques described in the above-mentioned US Provisional Patent Application 60/478,576.

As appropriate, techniques described herein are practiced in conjunction with methods and apparatus described in one or more of the following patent applications, all of which are assigned to the assignee of the present application and are incorporated herein by reference:

U.S. patent application Ser. No. 10/205,474, filed Jul. 24, 2002, entitled, "Electrode assembly for nerve control," which published as US Patent Publication 2003/0050677

U.S. Provisional Patent Application 60/383,157 to Ayal et al., filed May 23, 2002, entitled, "Inverse recruitment for autonomic nerve systems"

U.S. patent application Ser. No. 10/205,475, filed Jul. 24, 2002, entitled, "Selective nerve fiber stimulation for treating heart conditions," which published as US Patent Publication 2003/0045909

PCT Patent Application PCT/IL02/00068, filed Jan. 23, 2002, entitled, "Treatment of disorders by unidirectional nerve stimulation," and U.S. patent application Ser. No. 10/488,334, filed Feb. 27, 2004, in the US National Phase thereof U.S. patent application Ser. No. 09/944,913, filed Aug. 31, 2001, entitled, "Treatment of disorders by unidirectional nerve stimulation"

U.S. patent application Ser. No. 10/461,696, filed Jun. 13, 2003, entitled, "Vagal stimulation for anti-embolic therapy"

PCT Patent Application PCT/IL03/00430, filed May 23, 2003, entitled, "Electrode assembly for nerve control," which published as PCT Publication WO 03/099373

PCT Patent Application PCT/IL03/00431, filed May 23, 2003, entitled, "Selective nerve fiber stimulation for treating heart conditions," which published as PCT Publication WO 03/099377

U.S. patent application Ser. No. 10/719,659, filed Nov. 20, 2003, entitled, "Selective nerve fiber stimulation for treating heart conditions"

A PCT patent application filed May 23, 2004, entitled, "Selective nerve fiber stimulation for treating heart conditions"

A PCT patent application filed on even date herewith, entitled, "Applications of vagal stimulation"

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A treatment method, comprising:
applying an electrical current to a vagus nerve of a subject; and
modulating the current to cause fluctuation in atrial contractility sufficiently to reduce a risk of an occurrence of a thromboembolic event,
wherein modulating the current to cause the fluctuation in the atrial contractility comprises cycling between first and second stimulation periods, and:
during the first stimulation periods, configuring the current to cause a reduction in a force of contraction of atrial cells of the subject, and configuring the current so as to induce action potentials in the vagus nerve; and
during the second stimulation periods, configuring the current to cause an increase in the reduced force of contraction of the atrial cells, and configuring the current so as to block action potentials in the vagus nerve.

2. A method according to claim 1, wherein applying the current comprises identifying that the subject is suffering from atrial fibrillation (AF) and from increased risk of thromboembolic events, and applying the current responsively to the identifying.

3. A method according to claim 1, wherein applying the current comprises detecting an occurrence of atrial fibrillation (AF), and applying the current responsively to the detecting.

4. A method according to claim 1, wherein modulating the current comprises sensing at least one physiological variable of the subject, and synchronizing a commencement of at least one of the first and second stimulation periods with the sensed physiological variable.

5. A method according to claim 1, wherein applying the current comprises identifying that the subject is suffering from atrial fibrillation (AF), and applying the current responsively to the identifying.

6. A treatment method, comprising:
applying an electrical current to a vagus nerve of a subject; and
modulating the current to cause fluctuation in atrial contractility sufficiently to reduce a risk of an occurrence of a thromboembolic event,
wherein modulating the current to cause the fluctuation in the atrial contractility comprises cycling between first and second stimulation periods, and:
during the first stimulation periods, configuring the current to cause a reduction in a force of contraction of atrial cells of the subject; and
during the second stimulation periods, configuring the current to cause an increase in the reduced force of contraction of the atrial cells,
wherein modulating the current comprises sensing at least one physiological variable of the subject, and synchronizing a commencement of at least one of the first and second stimulation periods with the sensed physiological variable,
wherein the sensed physiological variable includes a QRS-complex of the subject, and wherein modulating the current comprises initiating each of the first stimulations period within about 50 milliseconds after an occurrence of the QRS-complex.

7. A method according to claim 6, wherein applying the current comprises identifying that the subject is suffering from atrial fibrillation (AF) and from increased risk of thromboembolic events, and applying the current responsively to the identifying.

8. A method according to claim 6, wherein applying the current comprises detecting an occurrence of atrial fibrillation (AF), and applying the current responsively to the detecting.

9. A method according to claim 6, wherein applying the current comprises identifying that the subject is suffering from atrial fibrillation (AF), and applying the current responsively to the identifying.

10. A treatment method, comprising:
    applying an electrical current to a vagus nerve of a subject; and
    modulating the current to cause fluctuation in atrial contractility sufficiently to reduce a risk of an occurrence of a thromboembolic event,
    wherein modulating the current to cause the fluctuation in the atrial contractility comprises cycling between first and second stimulation periods, and:
    during the first stimulation periods, configuring the current to cause a reduction in a force of contraction of atrial cells of the subject; and
    during the second stimulation periods, configuring the current to cause an increase in the reduced force of contraction of the atrial cells,
    wherein modulating the current comprises sensing at least one physiological variable of the subject, and synchronizing a commencement of at least one of the first and second stimulation periods with the sensed physiological variable,
    wherein the sensed physiological variable includes an expiration by the subject, and wherein modulating configuring the current comprises initiating each of the first stimulation periods within about 500 milliseconds after a beginning of the expiration.

11. A method according to claim 10, wherein applying the current comprises identifying that the subject is suffering from atrial fibrillation (AF) and from increased risk of thromboembolic events, and applying the current responsively to the identifying.

12. A method according to claim 10, wherein applying the current comprises detecting an occurrence of atrial fibrillation (AF), and applying the current responsively to the detecting.

13. A method according to claim 10, wherein applying the current comprises identifying that the subject is suffering from atrial fibrillation (AF), and applying the current responsively to the identifying.

14. A treatment method, comprising:
    applying an electrical current to a vagus nerve of a subject; and
    modulating the current to cause fluctuation in atrial contractility sufficiently to reduce a risk of an occurrence of a thromboembolic event,
    wherein modulating the current to cause the fluctuation in the atrial contractility comprises cycling between first and second stimulation periods, and:
    during the first stimulation periods, configuring the current to cause a reduction in a force of contraction of atrial cells of the subject; and
    during the second stimulation periods, configuring the current to cause an increase in the reduced force of contraction of the atrial cells,
    wherein modulating the current comprises sensing at least one physiological variable of the subject, and synchronizing a commencement of at least one of the first and second stimulation periods with the sensed physiological variable,
    wherein the sensed physiological variable includes diastole of the subject, and wherein modulating configuring the current comprises initiating each of the second stimulation periods substantially simultaneously with a portion of the diastole.

15. A method according to claim 14, wherein modulating the current comprises setting each of the first stimulation periods to have a duration of between about 100 milliseconds and about 1000 milliseconds.

16. A method according to claim 14, wherein modulating the current comprises setting each of the second stimulation periods to have a duration of between about 200 milliseconds and about 15 seconds.

17. A method according to claim 14, wherein modulating the current comprises configuring the current to have a first frequency during the first stimulation periods, and a second frequency during the second stimulation periods, the first frequency greater than the second frequency.

18. A method according to claim 14, wherein modulating the current comprises configuring the current to have a first amplitude during the first stimulation periods, and a second amplitude during the second stimulation periods, the first amplitude greater than the second amplitude.

19. A method according to claim 14, wherein applying the current comprises:
    applying the current during the first stimulation periods; and
    withholding applying the current during the second stimulation periods.

20. A method according to claim 14,
    wherein applying the current comprises applying the current in respective bursts in each of a plurality of cardiac cycles of the subject, and
    wherein modulating the current comprises configuring each pulse of each of the bursts to have a pulse width of at least a first pulse width during the first stimulation periods, and to have a pulse width of less than a second pulse width during the second stimulation periods, the first pulse width being greater than or equal to the second pulse width.

21. A method according to claim 14,
    wherein applying the current comprises applying the current in respective bursts in each of a plurality of cardiac cycles of the subject, and wherein modulating the current comprises configuring each of the bursts to have a number of pulses of at least a first number of pulses during the first stimulation periods, and to have a number of pulses of less than a second number of pulses during the second stimulation periods, the first number of pulses being greater than or equal to the second number of pulses.

22. A method according to claim 14, wherein applying the current comprises identifying that the subject is suffering from atrial fibrillation (AF) and from increased risk of thromboembolic events, and applying the current responsively to the identifying.

23. A method according to claim 14, wherein applying the current comprises detecting an occurrence of atrial fibrillation (AF), and applying the current responsively to the detecting.

24. A method according to claim 14, wherein applying the current comprises identifying that the subject is suffering from atrial fibrillation (AF), and applying the current responsively to the identifying.

* * * * *